(12) United States Patent
Barman et al.

(10) Patent No.: US 10,194,983 B2
(45) Date of Patent: *Feb. 5, 2019

(54) METHODS FOR THERAPEUTIC RENAL DENERVATION

(71) Applicant: Medtronic Ardian Luxembourg S.a.r.l., Luxembourg (LU)

(72) Inventors: Neil Barman, Menlo Park, CA (US); Howard Levin, Teaneck, NJ (US); Paul Sobotka, St. Paul, MN (US); Mark Gelfand, New York, NY (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/837,488

(22) Filed: Dec. 11, 2017

(65) Prior Publication Data
US 2018/0168723 A1 Jun. 21, 2018

Related U.S. Application Data

(63) Continuation of application No. 15/458,496, filed on Mar. 14, 2017, now Pat. No. 9,867,663, which is a
(Continued)

(51) Int. Cl.
*A61B 18/14* (2006.01)
*A61B 18/08* (2006.01)
(Continued)

(52) U.S. Cl.
CPC .......... *A61B 18/1492* (2013.01); *A61B 18/02* (2013.01); *A61B 18/04* (2013.01);
(Continued)

(58) Field of Classification Search
CPC .............. A61B 18/1492; A61B 18/082; A61B 2018/00702; A61B 2018/00791;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

WO WO-1994007446 A1 4/1994
WO WO-1995025472 A1 9/1995
(Continued)

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
(Continued)

*Primary Examiner* — Mark W Bockelman

(57) ABSTRACT

Methods for therapeutic renal denervation are disclosed herein. One aspect of the present application, for example, is directed to methods that block, reduce and/or inhibit renal sympathetic nerve activity to achieve a reduction in central sympathetic tone. Renal sympathetic nerve activity may be altered or modulated along the afferent and/or efferent pathway. The achieved reduction in central sympathetic tone may carry several therapeutic benefits across many disease states.

16 Claims, 33 Drawing Sheets

Related U.S. Application Data continuation of application No. 14/297,970, filed on Jun. 6, 2014, now Pat. No. 9,629,679, which is a continuation of application No. 13/034,595, filed on Feb. 24, 2011, which is a continuation-in-part of application No. 11/145,122, filed on Jun. 3, 2005, now Pat. No. 8,150,518, which is a continuation of application No. 10/408,665, filed on Apr. 8, 2003, now Pat. No. 7,162,303.

(60) Provisional application No. 61/385,879, filed on Sep. 23, 2010, provisional application No. 61/307,633, filed on Feb. 24, 2010, provisional application No. 60/442,970, filed on Jan. 29, 2003, provisional application No. 60/415,575, filed on Oct. 3, 2002, provisional application No. 60/370,190, filed on Apr. 8, 2002.

(51) Int. Cl.
*A61N 1/36* (2006.01)
*A61N 1/32* (2006.01)
*A61B 18/00* (2006.01)
*A61B 18/02* (2006.01)
*A61B 18/04* (2006.01)
*A61K 31/165* (2006.01)
*A61K 31/198* (2006.01)
*A61K 31/4168* (2006.01)
*A61K 31/506* (2006.01)
*A61K 49/00* (2006.01)

(52) U.S. Cl.
CPC .......... *A61B 18/082* (2013.01); *A61K 31/165* (2013.01); *A61K 31/198* (2013.01); *A61K 31/4168* (2013.01); *A61K 31/506* (2013.01); *A61K 49/0004* (2013.01); *A61N 1/327* (2013.01); *A61N 1/36057* (2013.01); *A61N 1/36117* (2013.01); *A61B 2018/00434* (2013.01); *A61B 2018/00577* (2013.01); *A61B 2018/00702* (2013.01); *A61B 2018/00791* (2013.01); *A61B 2018/00875* (2013.01); *A61B 2018/0212* (2013.01); *A61N 1/326* (2013.01)

(58) Field of Classification Search
CPC .. A61B 201/00875; A61B 2018/00577; A61B 2018/00434; A61N 1/36117; A61N 1/327
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Vvhayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |

(56) References Cited

U.S. PATENT DOCUMENTS

| | | |
|---|---|---|
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2009/0149849 A1 | 6/2009 | Lin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | | |
|---|---|---|---|
| WO | WO-1995031142 A1 | 11/1995 | |
| WO | WO-1997036548 A1 | 10/1997 | |
| WO | WO-1998042403 A1 | 10/1998 | |
| WO | WO-1999000060 A1 | 1/1999 | |
| WO | WO-2001022897 A1 | 4/2001 | |
| WO | WO-2001070114 A1 | 9/2001 | |
| WO | WO-2003022167 | 3/2003 | |
| WO | WO-2003/082080 | 10/2003 | |
| WO | WO-2005030072 A1 | 4/2005 | |
| WO | WO-2005041748 A2 | 5/2005 | |
| WO | WO-2005/110528 A1 | 11/2005 | |
| WO | WO-2006041881 A2 | 4/2006 | |
| WO | WO-2006105121 A2 | 10/2006 | |
| WO | WO-2007008954 A2 | 1/2007 | |
| WO | WO-2007078997 A2 | 7/2007 | |
| WO | WO-2008049084 A2 | 4/2008 | |

OTHER PUBLICATIONS

Avitall et al., "The creation of linear contiguous lesions in the atria with an expandable loop catheter," Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. 2465470, Granted Oct. 28, 2015, Date of Opposition Jul. 27, 2016, 34 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, Time, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Pieper, et al., "Design and Implementation of a New Computerized System for Intraoperative Cardiac Mapping" Journal of Applied Physiology, 1991, vol. 71 (4), pp. 1529-1539.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

U.S. Appl. No. 11/363,867, filed Feb. 27, 2006, 70 pp.

U.S. Appl. No. 60/813,589, filed Dec. 29, 2005, 62 pgs.

U.S. Appl. No. 60/852,787, filed Oct. 18, 2006, 112 pgs.

Ureter, https://en.wikipedia.org/wiki/Ureter, Jun. 2016, 6 pgs.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

(56) References Cited

OTHER PUBLICATIONS

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.

(56) References Cited

OTHER PUBLICATIONS

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dubuc, M., et al., "Feasibility of cardiac cryoablation using a transvenous steerable electrode catheter." J Intery Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery embolization with diluted hot contrast medium: An experimental study." J Vasc Interv Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-ind ustrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S. J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D. L., et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J. F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resis-

(56) References Cited

OTHER PUBLICATIONS tant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.

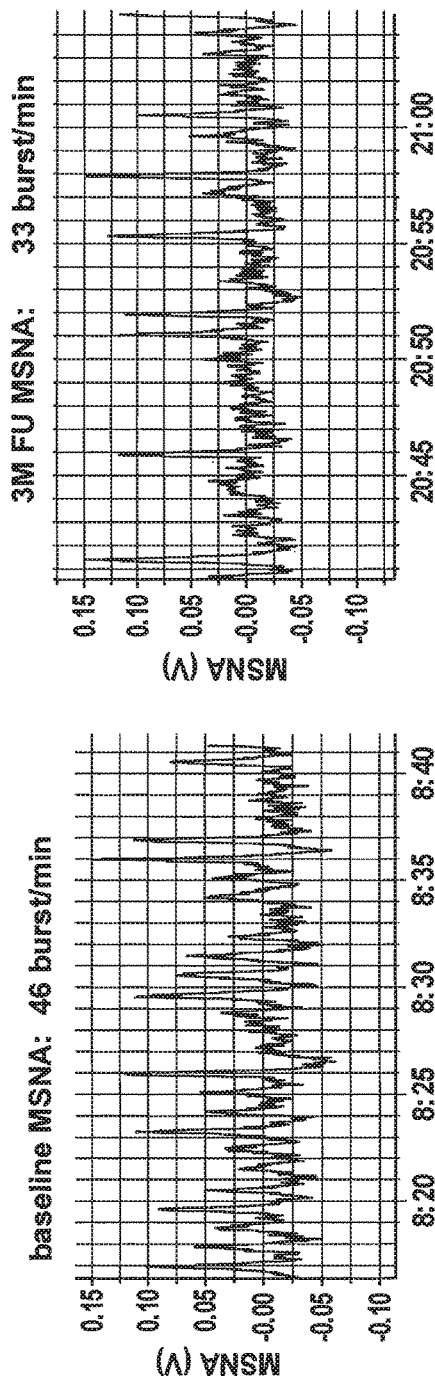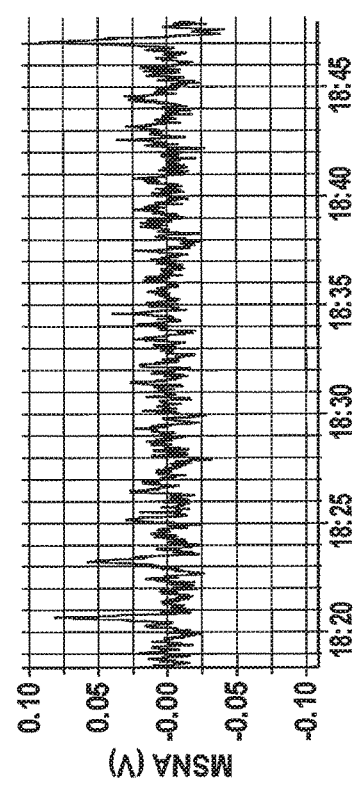

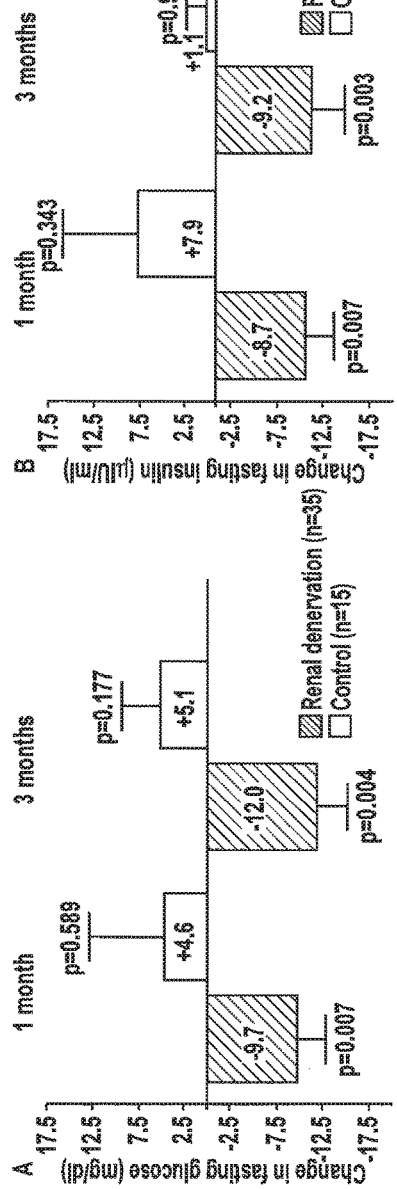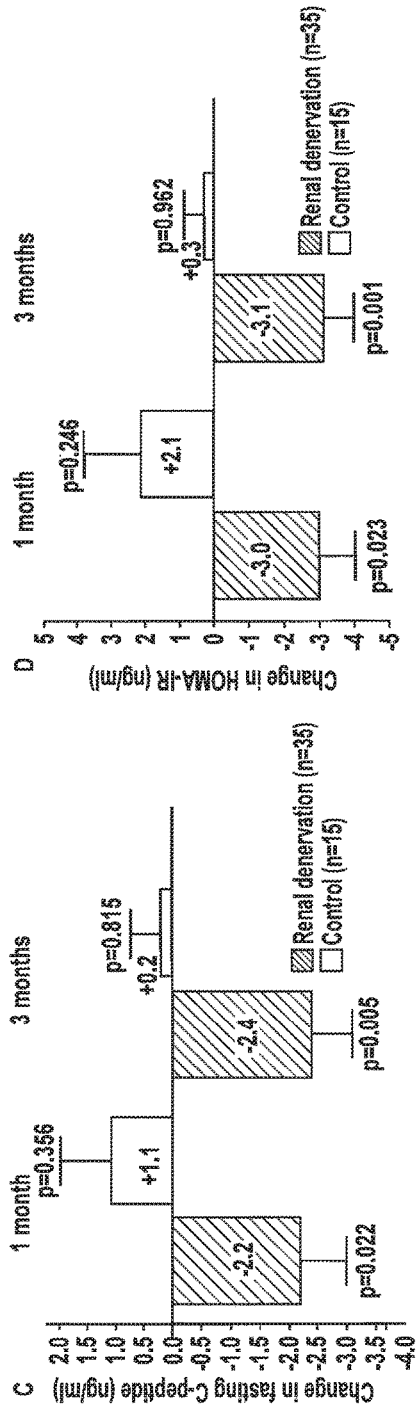
FIG. 16A
FIG. 16B
FIG. 16C
FIG. 16D ies for these conditions include non-pharmacological, pharmacological, and device-based approaches. Despite this variety of treatment options the rates of control of blood pressure and the therapeutic efforts to prevent progression of heart failure and chronic kidney disease and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

METHODS FOR THERAPEUTIC RENAL DENERVATION

REFERENCE TO RELATED APPLICATIONS

The present application is a Continuation application of U.S. patent application Ser. No. 15/458,496, filed on Mar. 14, 2017, now U.S. Pat. No. 9,867,663, which is a Continuation application of U.S. patent application Ser. No. 14/297,970, filed on Jun. 6, 2014, now U.S. Pat. No. 9,629,679, which is a Continuation application of U.S. patent application Ser. No. 13/034,595, filed on Feb. 24, 2011. U.S. patent application Ser. No. 13/034,595 claims the benefit of U.S. Provisional Application No. 61/385,879, filed on Sep. 23, 2010, and U.S. Provisional Application No. 61/307,633, filed on Feb. 24, 2010. U.S. patent application Ser. No. 13/034,595 is also a Continuation-in-Part application of U.S. patent application Ser. No. 11/145,122, filed on Jun. 3, 2005, now U.S. Pat. No. 8,150,518, which is a Continuation application of U.S. patent application Ser. No. 10/408,665, filed on Apr. 8, 2003, now U.S. Pat. No. 7,162,303, which claims the benefit of U.S. Provisional Application Nos. (a) 60/370,190, filed on Apr. 8, 2002, (b) 60/415,575, filed on Oct. 3, 2002, and (c) 60/442,970, filed on Jan. 29, 2003.

INCORPORATION BY REFERENCE

All publications, including issued patents, and patent applications mentioned in this specification are herein incorporated by reference to the same extent as if each individual publication or patent application was specifically and individually indicated to be incorporated by reference.

TECHNICAL FIELD

The technology disclosed in the present application generally relates to methods for therapeutic renal neuromodulation.

BACKGROUND

Hypertension, heart failure, chronic kidney disease, renal failure (end stage renal disease), diabetes, insulin resistance, metabolic disorder, and other conditions associated with hyperactivity of the sympathetic nervous system represent a significant and growing global health issue. Current therapies for these conditions include non-pharmacological, pharmacological, and device-based approaches. Despite this variety of treatment options the rates of control of blood pressure and the therapeutic efforts to prevent progression of heart failure and chronic kidney disease and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

Reduction of sympathetic nerve activity via renal neuromodulation can reverse these processes. Ardian of Mountain View, Calif., has discovered that an energy field, including and comprising an electric field, can initiate renal neuromodulation via denervation caused by irreversible electroporation, electrofusion, apoptosis, necrosis, ablation, thermal alteration, alteration of gene expression, or another suitable modality.

BRIEF DESCRIPTION OF THE DRAWINGS

In the drawings, the sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 10B is a graph illustrating baseline MSNA for the patient of FIG. 10A.

FIG. 10C is a graph illustrating 3-month MSNA for the patient of FIG. 10A.

FIG. 10D is a graph illustrating 12-month MSNA for the patient of FIG. 10A.

FIGS. 16A-16D show changes in fasting glucose (FIG. 16A), fasting insulin (FIG. 16B), fasting C-peptide (FIG. 16C) and HOMA-IR (FIG. 16D) for the patients and control group of FIG. 15.

DETAILED DESCRIPTION

Figure 1:
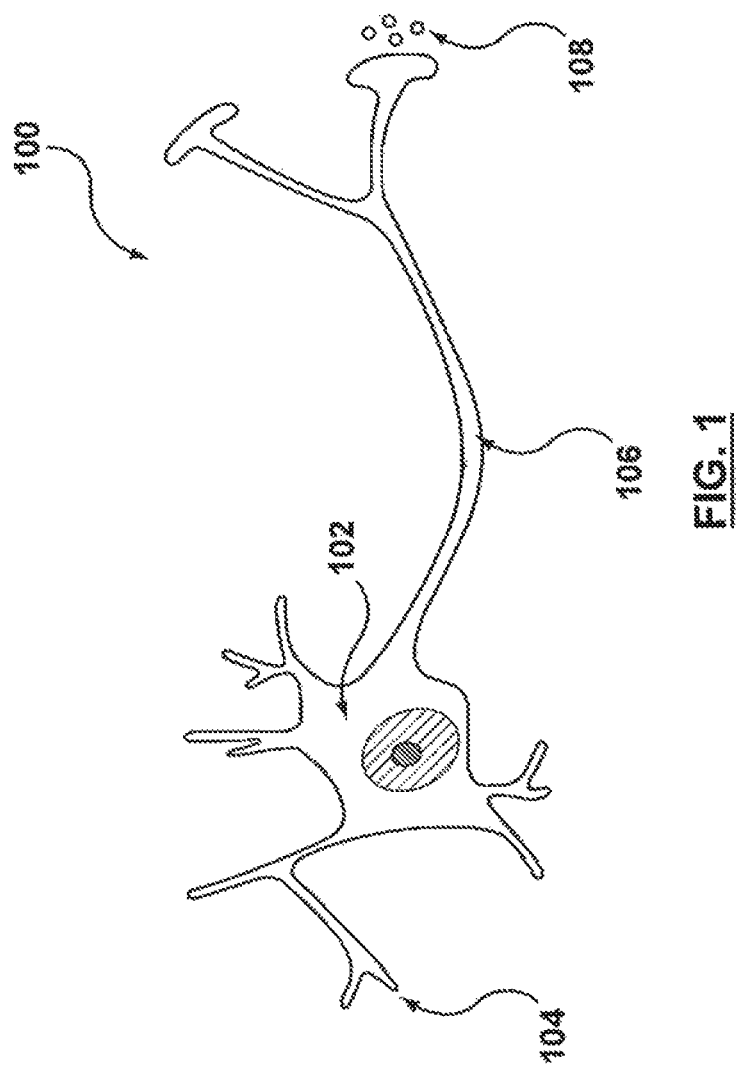
FIG. 1 is a schematic illustration of a human neuron.

The present disclosure describes methods for therapeutic renal neuromodulation and associated systems and methods. Many specific details of certain embodiments of the disclosure are set forth in the following description and in FIGS. 1-28 to provide a thorough understanding of these embodiments. Well-known structures, systems, and methods often associated with the disclosed technologies have not been shown or described in detail to avoid unnecessarily obscuring the description of the various embodiments of the disclosure. In addition, those of ordinary skill in the relevant art will understand that additional embodiments may be practiced without several of the details described below.

The following description includes four sections, each focused on a particular aspect of methods for therapeutic renal neuromodulation. Section 1 focuses on the pertinent anatomy and physiology. Section 2 focuses on measuring sympathetic activity and associated techniques. Section 3 focuses on chronic sympathetic activation and its relationship to essential hypertension, congestive heart failure, chronic kidney disease, renal failure, insulin resistance, diabetes, metabolic disorder, obesity, and sleep apnea. Section 4 focuses on therapeutic renal neuromodulation to reduce central sympathetic drive and sympathetic neural activity in a manner that treats a patient for at least one of the aforementioned diseases. Each of the following sections describes several embodiments of the corresponding methods, structures, and techniques that are the focus of that particular section. Overall methods and systems in accordance with other embodiments of the disclosure can include any of a wide variety of combinations and variations of the following embodiments.

I. Pertinent Anatomy and Physiology

A. Autonomic Nervous System

The autonomic nervous system (ANS) is comprised of the parasympathetic and sympathetic nervous systems. These systems work together to regulate visceral body functions including heart rate, blood pressure, respiration, digestion, body temperature, and urination. The ANS is always active at a basal level, primarily acting in an involuntary, reflexive manner to maintain homeostasis. The sympathetic and parasympathetic nervous systems involve networks of nerves connecting the brain, the spinal cord and the peripheral organs. These two systems regulate visceral body functions including respiration, cardiovascular activity, and energy balance.

B. Sympathetic Nervous System

Activation of the sympathetic nervous system (SNS) is typically associated with a "fight or flight" quick alarm or stress response that enables the body to perform strenuous physical activity, such as when fleeing from danger. Within seconds, the heart pumps more forcefully, the heart rate increases, blood is shunted from the GI tract to active muscles and the brain, and blood glucose increases to provide energy for increased cellular metabolism. Sympathetic drive is also a key regulator of the body's blood pressure and fluid balance, ensuring adequate blood supply for vital organs such as the brain when the body is fleeing from danger.

The sympathetic nervous system is balanced by the functions of the "rest and digest" parasympathetic nervous system (PNS), which promotes nutrient absorption from the GI tract and energy storage. While the SNS responds within seconds to environmental triggers, some effects of the parasympathetic nervous system may not be seen for hours. Most visceral organs have both sympathetic and parasympathetic innervation, though one system can dominate control of a given organ. The response to activation of the SNS and PNS is both neuronally and hormonally mediated. The hormonal contribution comes from the adrenal gland, which is activated by the SNS and PNS to release hormones such as epinephrine (adrenaline) into the bloodstream that can amplify the body's response to the neural stimulation. Together, the functions of the sympathetic and parasympathetic nervous systems enable the body to respond to environmental stimuli in a graded fashion instead of simply on or off.

The SNS is composed primarily of neurons. As shown in FIG. 1, for example, neurons 100 are composed of three parts: the cell body 102 where information is integrated, specialized projections 104 (i.e., dendrites) that bring information into the cell body 102, and a single projection 106 (i.e., axon) that takes information away from the cell body. Information is passed between neurons electrochemically across synapses, small gaps between axons 106 and dendrites 104. At a distal end of the pre-synaptic neuron's axon 106, chemicals termed neurotransmitters 108 are released, cross the synapse, and bind to cell surface receptors at a post-synaptic neuron (not shown). An electric potential is generated in the post-synaptic dendrite and spreads to the cell body, where the signal is integrated. The signal is relayed to the next neuron (not shown) by generating an electrical potential that travels down the corresponding axon, activating release of neurotransmitters at the distal end of the axon into the next synapse.

Axons are typically bundled together like the ropes of a cable; a large bundle can be visible to the naked eye and is often called a nerve fiber. A cluster of neurons and synapses is called a ganglion. Ganglions provide key relay points throughout the sympathetic nervous system. Although nerve signals may travel from one ganglia to another, many signals pass through only one ganglion. When considering the general ANS architecture, post-ganglionic neurons are those neurons that have their cell bodies in the ganglia and send axons directly out to the peripheral organs. All other neurons are termed pre-ganglionic neurons.

Figure 2:
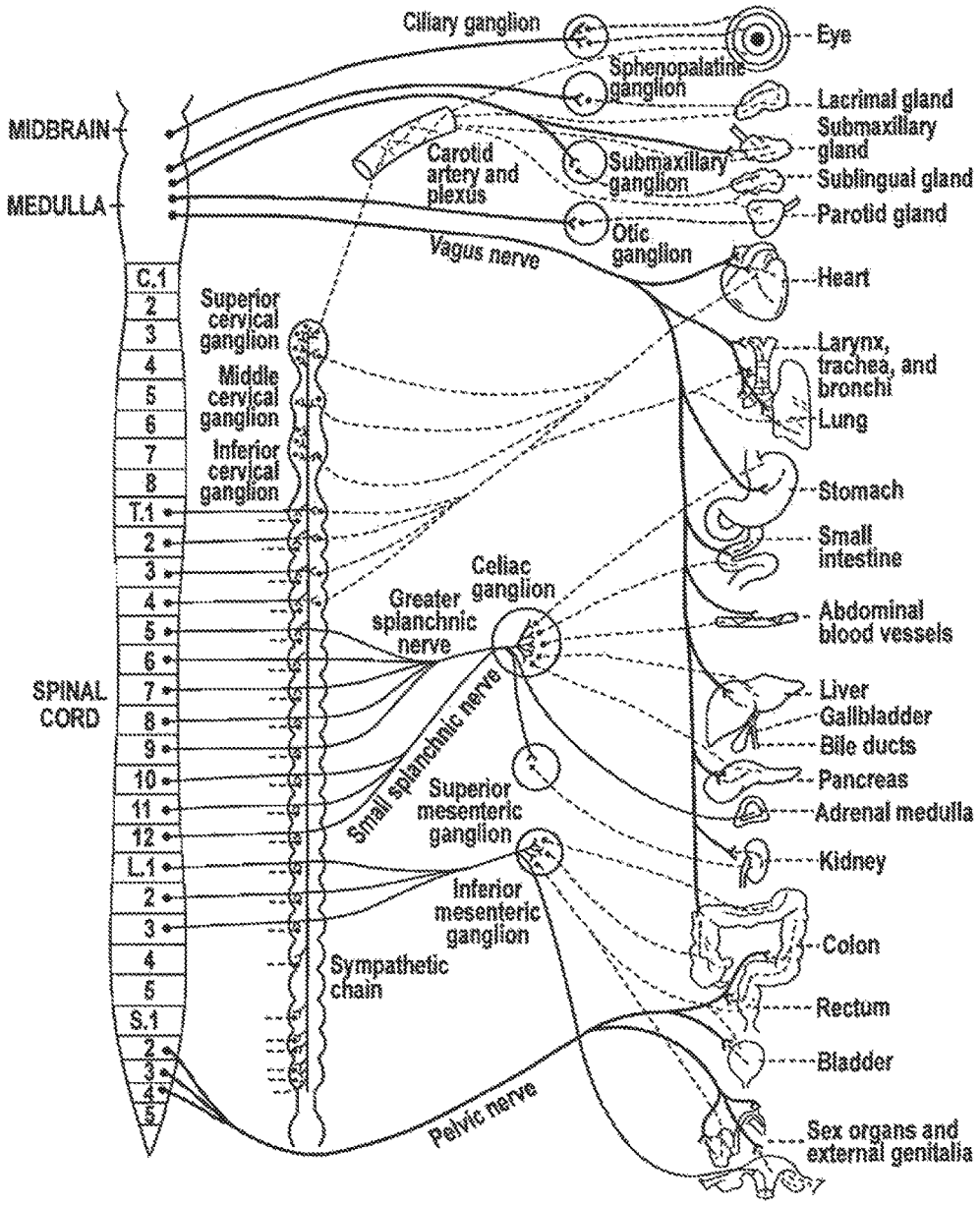
FIG. 2 is a conceptual illustration of a human sympathetic nervous system (SNS).

FIG. 2 is a conceptual illustration of a human SNS illustrating how the brain communicates with the body via the SNA. The nerves comprising the SNS enable bidirectional signal communication between the brain, spinal cord, and nearly every organ system. For example, signals from the periphery to the brain, termed afferent signals, travel within one neuron and carry information primarily about temperature or pain. In the opposite direction, efferent signals are primarily transmitted by a two neuron system; the first neuron originates in the brain and spinal cord, exits at the mid-lower back at spinal levels T1-L2 (the sympathetic thoracolumbar outflow) and synapses in a ganglia. The most prominent ganglia are those found parallel to the vertebral column at spinal levels T1-L2. These are grouped together as the sympathetic trunk. Post-ganglionic nerves from the sympathetic trunk primarily regulate the abdominal and thoracic visceral organs. Other important ganglia of the SNS include the cervical ganglion (regulates organs in the head and thorax), the celiac ganglion, and the mesenteric ganglia (regulates abdominal organs). Post-ganglionic nerves then transmit the signal directly to the peripheral organs.

Efferent neuronal signaling in the SNS is carried by two primary small molecule neurotransmitters: acetylcholine and norepinephrine. All preganglionic signals are mediated by acetylcholine, a chemical messenger that binds and activates cholinergic receptors on postganglionic neurons. Acetylcholine is primarily an activating neurotransmitter. In the brain, for example, acetylcholine improves attention, enhances sensory perceptions, and enhances memory and learning. Preganglionic release of acetylcholine stimulates postganglionic neurons, thereby promoting generation of electric potentials in the postganglionic neurons. Once stimulated, postganglionic neurons primarily use the neurotransmitter noradrenaline (norepinephrine). Norepinephrine binds to adrenergic receptors to directly stimulate peripheral organs. In the adrenal gland, SNS stimulation causes norepinephrine release into the blood, heightening the body's arousal and enhancing the SNS response.

Figure 3:
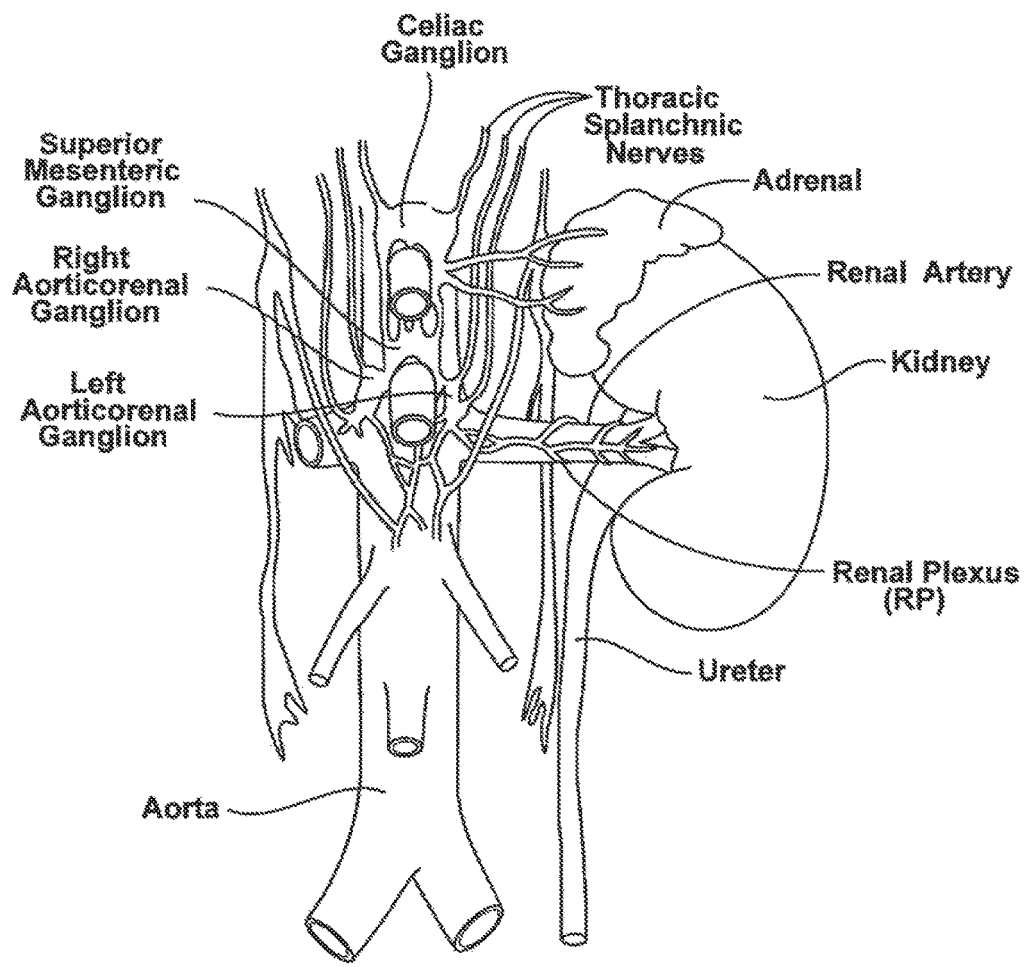
FIG. 3 is an enlarged anatomic view of nerves innervating a left kidney to form a renal plexus surrounding the left renal artery.

FIG. 3 is an enlarged anatomic view of nerves innervating a left kidney to form a renal plexus surrounding the left renal artery. Sympathetic communication between the CNS and the kidney is achieved via many neurons that travel from the sympathetic chain to innervate the kidney. Many of these nerves arise primarily from the celiac ganglion, the superior mesenteric ganglion, and the aorticorenal ganglion. From the ganglia, these fibers join together into a plexus of nerves that surround the renal artery. This is typically termed the renal plexus or renal nerve. The renal plexus or nerve is embedded within the adventitia (i.e., the outer wall) of the renal artery extending along the renal artery until it arrives at the substance of the kidney. There is also rich innervation of the kidney vasculature and of the tubular structures (nephrons) that comprise the filtering and concentrating functions of the kidney.

The renal plexus carries both afferent and efferent signals. As mentioned previously, afferent signals increase with temperature, pain, decreased renal blood flow, and intra-renal pathologies such as kidney hypoxia or ischemia. They are also influenced by the chemical composition of the urine; small signaling molecules such as adenosine are released into the urine when the kidneys are hemodynamically (i.e. too much or too little blood flow) or metabolically stressed. Afferent signals are carried by several different neurotransmitters including substance P, a molecule well known to participate in pain signaling. Signals from one kidney impact the renal sympathetic outflow and the functioning of both that kidney and the opposite (contralateral) kidney and also affect the brain. Central integration of the afferent signals in the posterior hypothalamus of the brain and in the spinal cord causes increased central sympathetic outflow.

Efferent renal nerve activity is stimulated by numerous inputs. As mentioned above, afferent signals from one kidney can cause increased efferent activity in that kidney as well as the contralateral kidney. This latter effect is known as the renorenal reflex. In addition, most stimuli of central sympathetic outflow also increase efferent renal nerve activity. These stimuli include infection, inflammation, and acute stress, which release chemical mediators that can act directly on the brain to increase central sympathetic outflow. In addition, feedback mechanisms such as the baroreceptor reflex can increase central sympathetic outflow. Baroreceptor sensors in the carotid arteries of the neck are sensitive to blood pressure. A fall in blood pressure causes a corresponding fall in baroreceptor activity, which stimulates increased sympathetic outflow.

C. SNS and Blood Pressure Regulation

The SNS plays a central role in blood pressure regulation. Blood pressure is a function of three main factors: (a) cardiac output (i.e., determined by the volume of blood pumped out of the heart per beat and the heart rate), (b) total blood volume, and (c) the resistance to flow in the blood vessels (i.e., how constricted or widened and stiff or flexible they are). Blood pressure can be simply conceptualized as analogous to the pressure in a garden hose; narrow hoses connected to a fire hydrant pumping large fluid volumes have high pressure. The SNS regulates all three of the factors that contribute to blood pressure, and can promote an acute state of elevated blood pressure that would be helpful in reacting to situations of high stress and/or danger.

Figure 4:
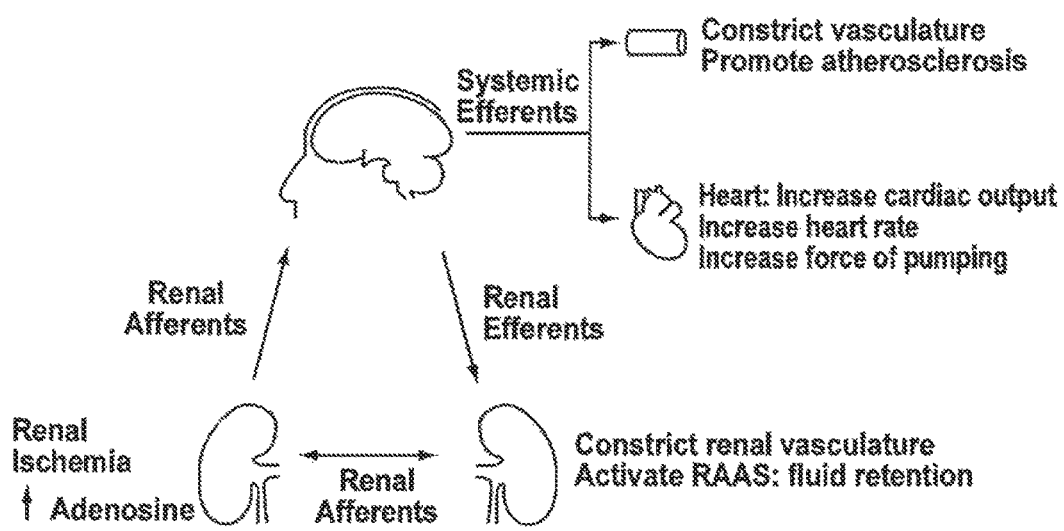
FIG. 4 is a conceptual illustration of a human body depicting neural efferent and afferent communication between the brain and kidneys.

FIG. 4 is a conceptual illustration of a human body depicting neural efferent and afferent communication between the brain and kidneys. As shown in FIG. 4, the sympathetic neural communication between the central nervous system and the heart, peripheral vasculature, and kidneys contribute to high blood pressure. For example, since heart muscle is innervated by sympathetic fibers, activation of the SNS stimulation of the heart can increase contractility, including the rate and force of pumping, thereby increasing cardiac output. The smooth muscle that lies in the wall of peripheral blood vessels is also innervated by sympathetic fibers. Sympathetic activation causes contraction of smooth muscle, resulting in constriction of the peripheral vessels. This constriction effectively narrows the diameter of these peripheral blood vessels, thereby increasing their resistance to flow and raising blood pressure. As described below, neural stimulation of the kidney activates the renin-angiotensin-aldosterone system, a hormonal system that can increase fluid retention and further constrict blood vessel diameter.

Figure 5:
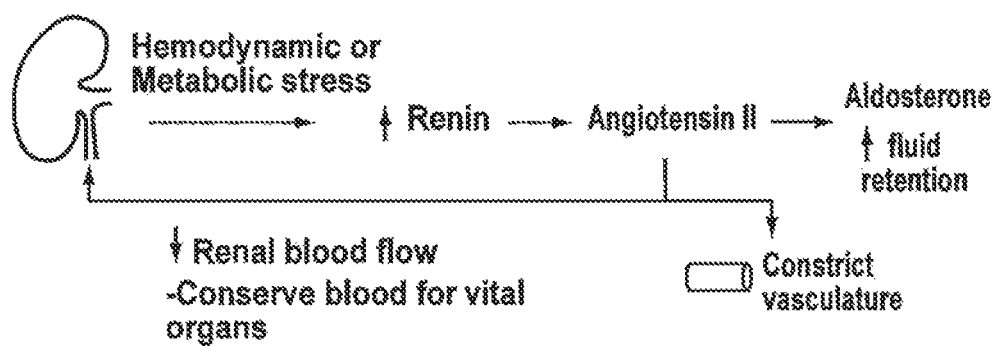
FIG. 5 is a conceptual illustration of a human renin-angiotensin-aldosterone system (RAAS).

Efferent renal sympathetic outflow activates the renin-angiotensin-aldosterone system. FIG. 5, for example, is a conceptual illustration of a human renin-angiotensin-aldosterone system (RAAS). The RAAS increases blood pressure and promotes fluid retention via the activity of multiple hormones and proteins. First, sympathetic neural signaling to the kidney and/or chemical signaling from specialized cells in the kidney induces the release of renin from the kidney. In turn, renin stimulates production of angiotensin II, a small protein released into the blood that directly causes blood vessels to constrict, thereby raising blood pressure. Angiotensin II also stimulates the adrenal glands to secrete aldosterone, a hormone that acts on the kidney to increase sodium and water retention. This fluid retention expands the blood volume, secondarily increasing blood pressure. As the blood pressure rises, efferent signaling to the RAAS falls, providing negative feed back to the system and preventing runaway high blood pressure levels.

II. Measuring Sympathetic Activity

SNS activity is often measured using methods including microneurography or norepinephrine spillover. Microneurography is the more direct method of the two to measure the level of sympathetic activity. It involves insertion of an electrode into the nerve to measure directly the action potentials from axons of sympathetic nerves. The electrode picks up signals from all neurons in the nerve bundle. An increased number and frequency of action potentials correlates with higher sympathetic outflow in that nerve bundle. Because this method requires a macroscopic nerve bundle into which the electrode can be placed, it cannot be used to represent the sympathetic stimulation to whole organs, which are often innervated by multiple nerves arranged in a meshlike plexus. Nevertheless, this method is well suited for measurement of sympathetic stimulation to peripheral muscles, which are often innervated by a single identifiable nerve. When microneurography is used in this case, the technique and measurable quantity is often termed "muscle sympathetic nerve activity," or MSNA.

Measurement of norepinephrine spillover is a less direct method of estimating SNS activity, but can be used to aggregate SNS outflow to whole organs and in the body as a whole. This method involves measuring the levels of the neurotransmitter norepinephrine released at a target organ. Increased neuronal firing corresponds with increased release of the neurotransmitter norepinephrine, which then can be measured via arterial and venous sampling of norepinephrine (a radioisotope of norepinephrine is also commonly used). For example, samples of blood from the renal artery can be measured for norepinephrine content and compared to the norepinephrine content in samples taken from the renal vein. Higher norepinephrine levels in the venous sample represent increased efferent sympathetic signaling to the kidney.

Overall sympathetic activity is estimated by measuring norepinephrine levels in the central veins draining from the body into the heart, termed "whole body norepinephrine levels." It can be especially useful to measure norepinephrine spillover in specific organs as sympathetic outflow is non-uniform and can vary significantly to different organs.

III. Chronic Sympathetic Activation

While acute activation of the SNS is an appropriate response to maintaining survival, chronic sympathetic activation is a maladaptive response. Without being bound by theory, it is thought that sensory afferent signals originating from the kidneys are often major contributors to initiate and sustain elevated central sympathetic outflow. With chronic stimulation, the body sets a new homeostasis where higher SNS outflow is the norm. This new homeostasis, however, is harmful to the body. Malfunction of the renal sympathetic nervous system and chronic sympathetic activation play a key role in the development and progression of diseases such as essential hypertension, chronic kidney disease, heart failure, insulin resistance and diabetes, among others. As described below in greater detail, derangement of end organs drives further SNS overactivity, contributing to a vicious cycle of SNS overactivity, hypertension, and end organ damage.

A. Chronic SNS Activity in Essential Hypertension

Essential hypertension is commonly initiated and sustained by sympathetic nervous system overactivity. Indeed, it is thought that nearly 50% of all cases of essential hypertension have a neurogenic cause. Patients diagnosed with essential hypertension also have elevated heart rate, cardiac output and renovascular resistance (due to constriction of the vessels leading up to and within the kidney), all of which are consistent with elevated sympathetic drive. It is thought that both tonic overstimulation and impaired negative feedback contribute to chronic SNS overactivity. However, the mechanisms for these factors is not yet fully understood, though the actions of hormones and proteins such as angiotensin II, insulin, and leptin are thought to be major players. Deranged levels of these hormones are likely caused by a combination of genetic factors, metabolic stressors such as diet or toxin exposure, environmental factors such as stress and anxiety, and organ damage or dysfunction.

In addition to increased central sympathetic drive, the renal sympathetic nerves specifically play a disproportionately larger role in the pathogenesis of essential hypertension. Efferent renal sympathetic signaling, as measured by norepinephrine spillover, is 2-3 times greater in patients with essential hypertension compared to normal patients. Persistent efferent signaling worsens hypertension, as it increases renal vascular resistance, reduces renal blood flow, and activates the RAAS. These effects would all contribute to further increasing SNS activity, exacerbating and perpetuating hypertension.

The cornerstone of anti-hypertension pharmacologic treatment is to break the cycle of sympathetic drive, hypertension and end organ damage. These drugs include ACE inhibitors and angiotensin receptor blockers (ARBs) that block the RAAS, beta blockers that reduce renin release and heart contractility, diuretics that promote urine production to reduce the total fluid load on the heart, and less commonly, centrally acting sympatholytics such as clonidine and moxonidine. These anti-hypertensive drugs have been shown to lower blood pressure, reduce patient hospitalizations, and improve patient mortality. Many of these drugs have also been shown to be renoprotective, limiting the progressive loss of renal function that commonly occurs with chronic hypertension. Despite the efficacy of pharmacological treatment, significant limitations exist with even the most current strategies. Some of these drawbacks, for example, include adverse effects, poor compliance, and the cost and complexity of ongoing follow up care.

The drawbacks of pharmaceutical intervention have created a classification of patients who are obtaining treatment, but are not able to manage their blood pressure to target. It is estimated that 40% of the patients on hypertensive medications are "treated but uncontrolled," with blood pressure levels in excess of 140 systolic and 90 diastolic. Failure to control high blood pressure is attributed to several factors, including poor adherence to the therapeutic plan, being overweight, volume overload due to high sodium intake, and undiscovered secondary causes of hypertension. For example, poor adherence to the therapeutic plan may be due to a patient's lack of discipline, frustration with medication side effects (e.g., impotence), or both. Additional challenges faced in addressing this epidemic are lack of access to regular health care and a disproportionate incidence of hypertension among racial and ethnic minorities.

Patients who are unable to achieve an adequate blood pressure reduction from lifestyle change and are resistant to drug therapy have no other means within modern medicine for bringing their blood pressure within control. Resistant or refractory hypertension is defined as blood pressure that remains above goal in spite of the concurrent use of three antihypertensive agents of different classes or patients whose blood pressure is controlled but requires four or more medications to do so.

Given the challenges faced by many patients in treating their hypertension with pharmacology, some have sought treatment via surgical intervention. More radical surgical methods to cut the thoracic, abdominal or pelvic sympathetic nerves at the level of the sympathetic chain has also been shown to be effective in reducing levels of essential hypertension. Such procedures, however, are highly invasive and associated with high perioperative morbidity and mortality, including bowel, bladder and erectile dysfunction and severe hypotension when patients stood up abruptly. Given the considerable collateral damage mentioned above, such surgical procedures are no longer performed.

B. Chronic SNS Activity in Congestive Heart Failure (CHF)

Many patients with essential hypertension progress to congestive heart failure, a condition where the heart's efficiency decreases as the heart fails to pump sufficient blood out to the body's other organs. As with hypertension, SNS overdrive contributes to the development and progression of CHF. Norepinephrine spillover from the kidney and heart to the venous plasma is even higher in CHF patients compared to those with essential hypertension. Chronic SNS stimulation overworks the heart, both directly as the heart increases its output and indirectly as a constricted vasculature presents a higher resistance for the heart to pump against. As the heart strains to pump more blood, left ventricular mass increases and cardiac remodeling occurs. Cardiac remodeling results in a heterogenous sympathetic activation of the heart which further disrupts the synchrony of the heart contraction. Thus, remodeling initially helps increase the pumping of the heart but ultimately diminishes the efficiency of the heart. Decrease in function of the left ventricle further activates the SNS and the RAAS, driving the vicious cycle that leads from hypertension to CHF.

Further, renal sympathetic activation worsens the progression of CHF. As CHF worsens, fluid is retained by the kidney and backs up from the heart, leading to the common symptoms seen with CHF including swelling of the legs, shortness of breath due to backup of blood into the lungs, and reduced ability to exercise as the heart fails to pump sufficient blood during periods of activity.

Heart failure is often treated with therapies similar to those described above used to treat essential hypertension. For example, ACE inhibitors, beta blockers, and diuretics are first line agents that have been shown to reduce mortality and hospitalizations.

C. Chronic SNS Activity in Chronic Kidney Disease and Renal Failure

Chronic hypertension may also lead to chronic kidney disease, which can lead to renal failure. An initial insult such as high blood pressure can directly damage the kidney. The insult can initially cause impaired filtration from the kidney, and may ultimately lead to irreparable damage to the kidney. Initial kidney damage increases renal afferent signaling through accumulation of adenosine in the kidney. As mentioned above, increased afferent activity can increase central sympathetic drive, thereby increasing efferent sympathetic signaling to the kidneys. This generally leads to activation of the RAAS and sodium and fluid retention. However, fluid retention combined with persistent hypertension places higher filtration and reabsorption demands on both the remaining healthy kidney and the damaged kidney, thus exposing the damaged kidney to further damage and placing the remaining healthy kidney at high risk for damage. The progression of chronic kidney disease may lead to renal failure, also known as end stage renal disease (ESRD), which is characterized as the complete failure of the kidney to remove wastes or concentrate urine.

Glomerular filtration rate (GFR), the rate at which the kidney filters blood, is commonly used to quantify kidney function and, consequently, the extent of kidney disease in a patient. Individuals with normal kidney function exhibit a GFR of at least 90 mL/min with no evidence of kidney damage. The severity of chronic kidney disease is generally characterized by several stages. For example, patients with stage 1 chronic kidney disease (CKD1) have a GFR of 90 mL/min or higher and also show evidence of kidney damage such as proteinuria (i.e., protein in the urine). Stage 2 (CKD2) is characterized by a GFR of 60 to 89 mL/min. In patients with moderate kidney disease, or Stage 3 (CKD3), the GFR is usually around 30 to 59 mL/min. Stage 4 (CKD4) is considered severe, with GFR between 15 and 20 mL/min. A GFR below 15 mL/min indicates that the patient has ESRD and is in complete kidney failure (CKD5).

Sympathetic overactivity is a hallmark of patients with chronic kidney disease and contributes to the development of ESRD, increasing with worsening kidney function. Without being bound by theory, it is believed that organ dysfunction, such as a failing or diseased kidney, may result in increased afferent neural signaling to the central nervous system which triggers and/or perpetuates activation of the SNS and increased central sympathetic drive. In support of this belief, studies have demonstrated that MSNA is higher in patients with ESRD compared to normal patients.

The treatment of chronic kidney disease primarily involves preventing or slowing the progression of renal dysfunction and treatment of any other conditions such as hypertension or diabetes that may contribute to the worsening of kidney function. In patients with hypertension, blood pressure control below 130/80 is the most effective single intervention to limit the progression of chronic kidney disease. Drugs such as ACE inhibitors and beta blockers have been shown to slow the progression of kidney damage while also controlling blood pressure. Central sympatholytic drugs such as moxonidine have also been investigated. In one such study, for example, moxonidine used as an add-on therapy in chronic renal failure patients was shown to stop the progression of renal failure, but to have limited effect on blood pressure. Data accordingly remains limited as to the efficacy of central sympatholytic drugs in chronic kidney disease and renal failure.

D. Chronic SNS Activity in Obesity and Sleep Apnea

It has been generally shown that obese individuals are more sympathetically activated. Without being bound by theory, it is believed that sympathetic activation in obesity is at least partially mediated by increased levels of insulin, leptin, and angiotensin II, and decreased levels of adiponectin. Sleep apnea also frequently accompanies obesity and has been shown to increase sympathetic and renal sympathetic activity. A state of sympathetic overactivity can also be accompanied by altered perfusion of skeletal muscle and the liver, both of which are important in glucose handling and glycogen storage.

Without being bound by theory, it is also generally believed that sleep apnea is associated with increased central sympathetic drive and impaired baroreflex sensitivity. Sleep apneas are generally categorized as obstructive or central in origin. Central sleep apnea occurs when the brain's respiratory control centers are imbalanced during sleep and the brain, consequently, temporarily stops sending signals to the muscles that control breathing, thereby causing moments of stopped breathing during sleep. Obstructive sleep apnea is characterized by obstruction of the patient's airway caused by collapsing walls of soft tissue. Airway narrowing leading to obstructive sleep apnea is often seen in overweight or obese patients, who tend to have excess mass in their neck regions. The oxygen deprivation (hypoxia) resulting from sleep apnea can cause severe conditions associated with respiratory and cardiovascular function.

Although obstructive sleep apnea is considered to be much more common than central sleep apnea, many apneic episodes display both central and obstructive features. The hypoxia resulting from repetitive apneic episodes may cause activation of the SNS. More specifically, the CNS responds to this hypoxia by elevating central sympathetic tone to increase perfusion to key organs, thereby causing elevations in blood pressure. Although elevated central sympathetic drive can result from sleep apnea, it may also contribute to the obesity and brain dysfunction that precipitate obstructive sleep apnea and central sleep apnea, respectively.

E. Chronic SNS Activity in Insulin Resistance, Diabetes, and Metabolic Disorder

SNS overactivity correlates with derangements in the metabolic homeostasis of the body, and can lead to metabolic syndrome, a combination of conditions that increases a person's risk for heart disease, stroke, and diabetes. The conditions that make up the metabolic syndrome include increased blood pressure, elevated insulin levels, central obesity, and abnormal cholesterol levels. Patients with diabetes mellitus have higher levels of total body norepinephrine spillover, suggesting that insulin resistance and central SNS overactivity are correlated.

A vicious cycle exists whereby insulin resistance promotes increased SNS activity, which in turn promotes increased insulin levels and further insulin resistance. It is not fully understood, however, which initiates the progression of disease. Infusion of insulin to acutely elevate insulin levels results in an increase in overall sympathetic outflow, as measured directly in muscle sympathetic nerves. This is thought to occur by several mechanisms. First, insulin acts directly on the brain to increase sympathetic drive. Insulin also decreases the breakdown of norepinephrine, increasing signaling by the sympathetic nervous system. Further, insulin dilates the peripheral blood vessels, causing an initial drop in central blood pressure. This is then compensated for by an increase in sympathetic outflow to increase the central blood pressure.

Alternatively, chronic sympathetic activity may be the driver of insulin resistance and metabolic syndrome. Vasoconstriction accompanying elevated circulating norepinephrine levels may deprive skeletal muscle from access to both glucose and insulin. Under normal conditions, skeletal muscle is responsible for a large percentage of total body glucose consumption and storage (in the form of glycogen). Sympathetic activity, however, promotes release of glucose and fats into the blood, which then trigger higher insulin release in the blood. Further, sympathetic drive promotes changes in the metabolic state of the peripheral muscles such that higher levels of glucose and insulin are required in order to achieve appropriate muscle response.

IV. Therapeutic Renal Neuromodulation

The physiology described above suggests an integral role between central sympathetic activity and the renal nerves in the development of several clinical conditions, including hypertension, metabolic syndrome, diabetes, insulin resistance, left ventricular hypertrophy, chronic and end stage renal disease, and/or heart failure. It is accordingly expected that renal neuromodulation e.g., via denervation of tissue containing renal nerves, may be valuable in the treatment of these diseases. More specifically, neuromodulation of afferent sensory nerves can reduce the systemic sympathetic drive through direct effect on the brain, thus reducing the sympathetic outflow to other organs such as the heart and the vasculature. Further, neuromodulation of efferent sympathetic nerves is expected to reduce inappropriate renin release, salt and water retention, and limit the progression of the aforementioned conditions.

A method has been recently developed to selectively modulate the renal afferent and efferent sympathetic nerves that lie within and alongside the adventitia (i.e., outer wall) of the renal arteries. Modulation of such nerves may be achieved using a variety of techniques. For example, an energy field including and comprising an electric field can initiate renal neuromodulation via denervation caused by irreversible electroporation, electrofusion, apoptosis, necrosis, ablation, thermal alteration, alteration of gene expression, or another suitable modality.

Figure 6:
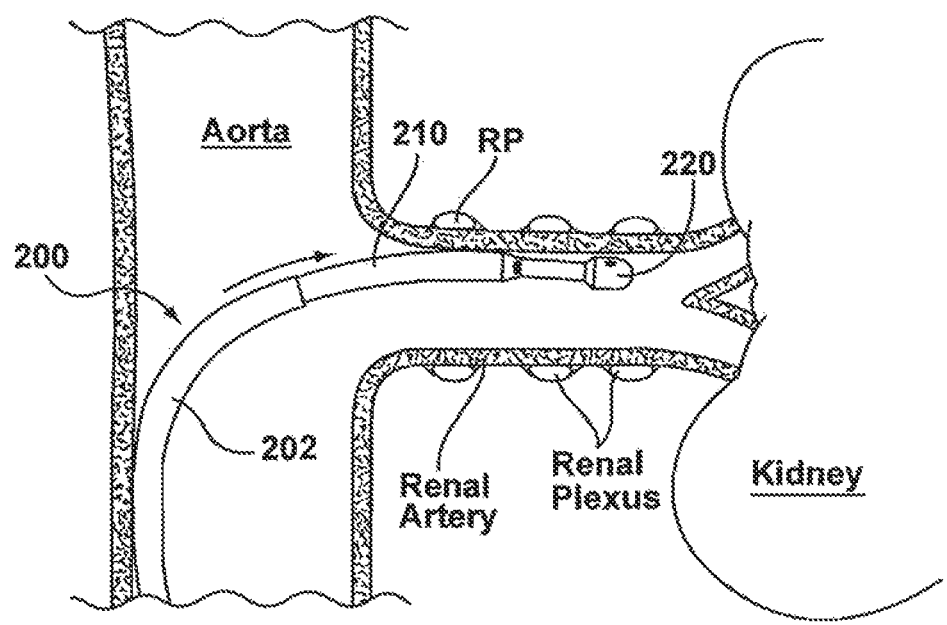
FIG. 6 is a detailed anatomic view of a catheter-based treatment device positioned within a renal artery and configured for therapeutic renal neuromodulation.

Several embodiments of this procedure involve discrete low-dose radiofrequency ablation of the target nerves via a radiofrequency (RF) emitting catheter placed on the inside wall of the renal artery. FIG. 6, for example, is a detailed anatomic view of a catheter-based treatment device 200 positioned within a renal artery of a patient and configured for renal neuromodulation in accordance with one embodiment of the disclosure. The device 200 can be deployed using a conventional guide catheter or pre-curved renal guide catheter 202. The device 200 can be introduced via the guide catheter 202 through the common femoral artery or, alternatively, through a brachial/radial approach, and advanced to the renal artery under guidance (e.g., fluoroscopic imaging guidance).

A flexible, controllable elongated shaft 210 of the treatment device 200 carries a thermal heating element 220, and thermal energy can be applied via the thermal heating element 220 to one or more target treatment sites along a length of the renal artery. The target treatment sites can be spaced longitudinally and rotationally along the length of the renal artery. Individual treatments can include, for example, ramped low power RF energy delivery (e.g., about 5 to 8 watts) for a selected period of time (e.g., two minutes). Blood flow through the renal artery can help minimize surface and/or endothelial injury to the target treatment sites. Further, focal ablations spaced apart from each other along the vessel allow for rapid healing. In one embodiment, up to six treatments are applied along the length of the renal artery beginning from where the renal artery branches off the aorta and ending at the kidney itself. In other embodiments, however, a different number of treatments may be applied and the treatment sites may have a different arrangement relative to each other. After all the treatments are completed, the treatment device 200 is removed from the patient. Various embodiments of methods, apparatuses, and systems for performing renal neuromodulation are described in greater detail in U.S. patent application Ser. No. 12/545,648, filed Aug. 21, 2009, and Patent Cooperation Treaty (PCT) Application No. PCT/US09/69334, filed Dec. 22, 2009, both of which are incorporated herein by reference in their entireties.

Other techniques or approaches for renal neuromodulation may also be administered to achieve the therapeutic benefits described herein. For example renal neuromodulation can be achieved via a pulsed electric field or intravascular electroporation. In still another example, U.S. Pat. No. 6,978,174 describes neuromodulation via delivery of neuromodulatory agents. In yet another example, U.S. Pat. No. 7,620,451 describes neuromodulation via an intra-to-extravascular approach. These patent references are incorporated herein by reference in their entireties.

A. Therapeutic Renal Neuromodulation in the Treatment of Hypertension

Figure 7:
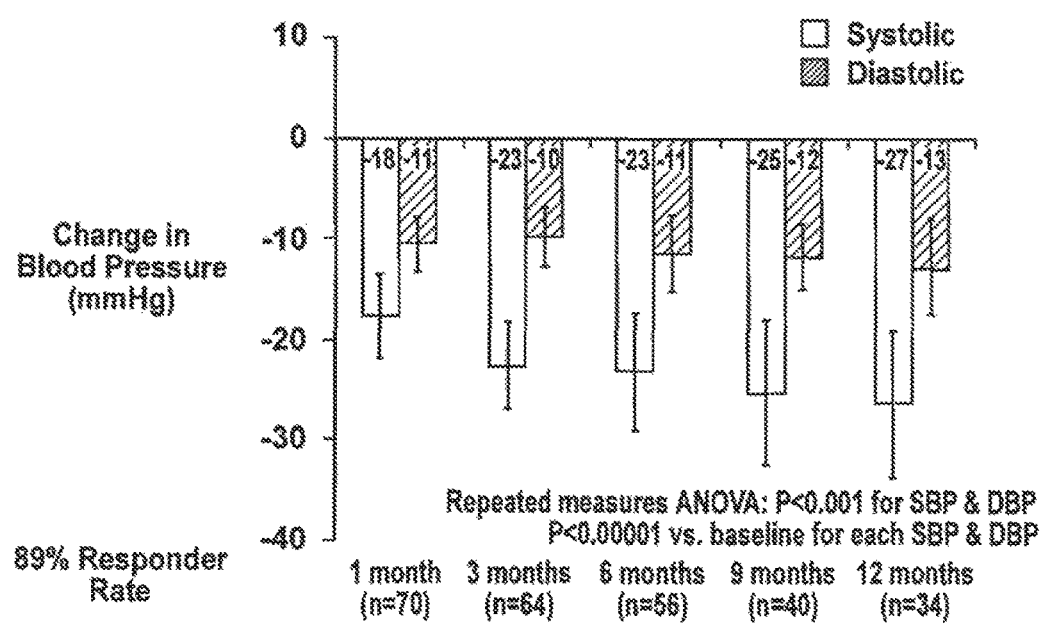
FIG. 7 is a diagram illustrating changes in blood pressure for patients with resistant essential hypertension who underwent therapeutic renal neuromodulation.

In one particular example, therapeutic renal neuromodulation was performed on 70 patients diagnosed with resistant essential hypertension, wherein each patient had systolic blood pressure of at least 160 mm Hg despite taking at least three anti-hypertensive medications. Without being bound by theory, the therapy was found to decrease blood pressure and central sympathetic drive in a significant majority of the patients. Referring to FIG. 7, for example, renal neuromodulation was found to lower systolic blood pressure by 18 mm Hg one month after treatment, and by 27 mm Hg at 12 months after treatment. This result is comparable in scale and more effective than what patients typically experience with the most common anti-hypertension pharmacologic drugs, which typically only lower systolic blood pressure by about 10 mm Hg when used alone. In the present study, 89% of the patients responded to therapy with more than a 10 mm Hg reduction of systolic blood pressure.

Measurements of norepinephrine spillover, as described above, taken in a subset of these patients confirmed a decrease in renal norepinephrine spillover from the kidney by 47%, indicating decreased sympathetic drive in the kidney. Whole-body norepinephrine levels (i.e., a measure of "total" sympathetic activity), fell by nearly 50% after renal nerve ablation. Measurement of muscle sympathetic nerve activity showed a drop of 66% over 6 months, further supporting the conclusion that total sympathetic drive was reduced by the renal denervation procedure.

These initial measurements suggest that renal neuromodulation or denervation is an effective method to reduce central sympathetic drive, renal sympathetic drive, and blood pressure to treat hypertension, particularly in patients that are resistant or refractory to pharmacological treatment. The data also suggests that the effectiveness of renal denervation is comparable and potentially superior to that of typical anti-hypertension pharmaceuticals when used alone to reduce systolic blood pressure levels. As further illustrated in FIG. 7, renal denervation had a durable effect on blood pressure as a significant decrease in blood pressure for more than 12 months after treatment was observed in most patients. In contrast with these results associated with renal neuromodulation, anti-hypertensive medications are typically only effective when the medications are continued. Further, initial animal studies suggested that ablated nerves would regenerate and re-innervate the ablated region, and possibly limit the effect and durability of the renal denervation procedure on central hypertension. Such re-innervation, however, was not observed in humans. As illustrated in FIG. 7, the treatment has exhibited significant durability, with measured blood pressures for many of the patients remaining below initial levels at 12 months following procedure.

In another example, therapeutic renal neuromodulation was assessed in a multicenter, prospective, randomized, controlled, clinical trial to demonstrate the effectiveness of catheter-based renal denervation for reducing blood pressure in patients with uncontrolled hypertension. 100 patients were randomized to a treatment with renal denervation (n=49) vs. control (n=51). Each patient had systolic blood pressure of at least 160 mm Hg (or ≥150 with type II diabetes mellitus) despite taking at least three anti-hypertensive medications.

Figure 8:
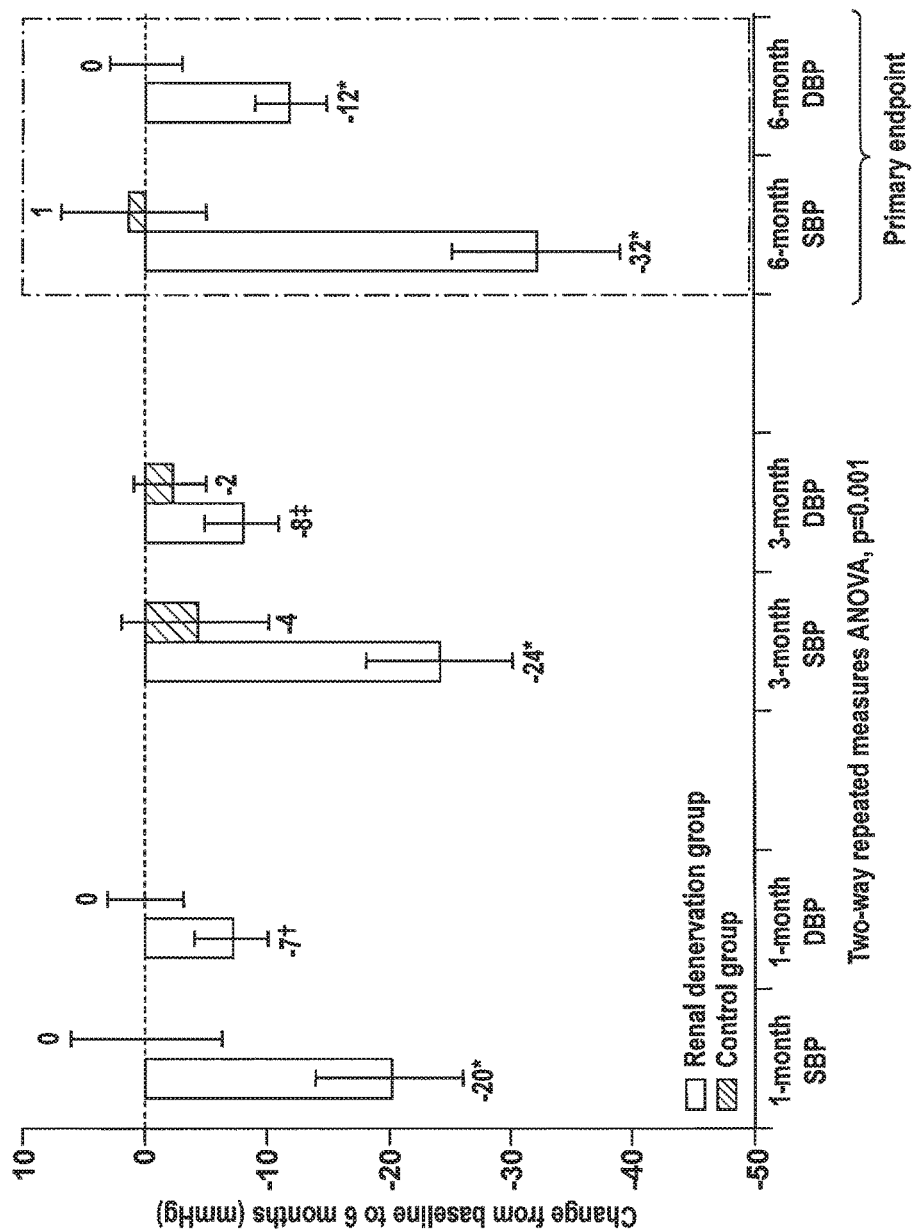
FIG. 8 is a diagram illustrating changes in blood pressure for patients with resistant essential hypertension who underwent therapeutic renal neuromodulation compared to a control group.

Without being bound by theory, the treatment group was found to have a significant reduction in blood pressure compared to the control group. Referring to FIG. 8, for example, at 6 months after treatment renal neuromodulation was found to reduce blood pressure by 32/12 mm Hg (SD 23/11) from 178/96 mm Hg (SD 18/16) at baseline (p<0.0001 for systolic and diastolic blood pressure). In comparison, the control group changed by 1/0 mm Hg (SD 21/10) from 178/97 mm Hg (SD 17/16) at baseline (p=0.77 for systolic blood pressure, p=0.83 for diastolic blood pressure). Therefore, the treatment group obtained a 33/11 mm Hg reduction in blood pressure compared to the control group (p<0.0001) during the 6 month follow-up. This larger, randomized, controlled trial supports the conclusions of the previous study that catheter-based renal denervation is an effective method to reduce blood pressure in patients that are resistant or refractory to pharmacological treatment.

B. Therapeutic Renal Neuromodulation in the Treatment of Congestive Heart Failure (CHF)

As previously described, congestive heart failure may be associated with elevated SNS and hypertension. The present inventors have discovered that therapeutic renal denervation may attenuate elevated central sympathetic tone, reduce hypertension, and have a beneficial effect on the heart which may reduce or stop the progression to CHF. Twelve patients diagnosed with resistant essential hypertension were treated with therapeutic renal denervation and their hearts were imaged with MRI to assess left ventricular mass index (LVMI). LVMI is a method of quantifying Left Ventricular Hypertrophy, or the enlargement of the left ventricle, which is an indication of the progression toward CHF. In this study LVMI was reduced after six months from 78.4 to 62.1 g/m² (−21%, p=0.044). This indicates that the wall thickness of the muscle of the left ventricle decreased, likely due to decreased pumping effort resulting from lower blood pressure and improved central sympathetic tone. The measured reduction in left ventricular mass indicates that renal neuromodulation/denervation therapy may assist in LVH regression, thereby providing a potential treatment for patients suffering from or at risk of diastolic heart failure.

Figure 9:
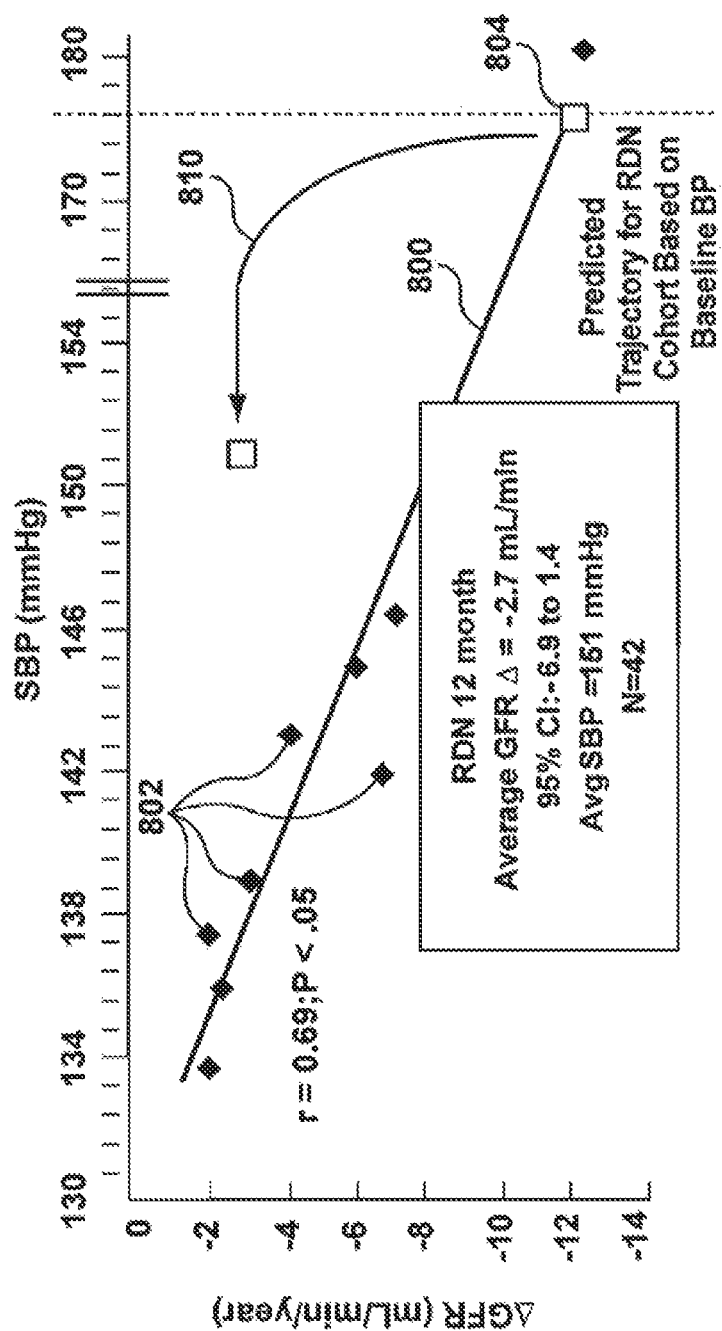
FIG. 9 is a graph illustrating changes in blood pressure and a renoprotective element for patients who underwent therapeutic renal neuromodulation.

C. Therapeutic Renal Neuromodulation in the Treatment of Chronic Kidney Disease and Renal Failure As described previously, it is well known that chronic high blood pressure precipitates declining kidney function. It is also understood that worsening hypertension will increase the rate of decline of kidney function. FIG. 9 provides a graphical depiction of the increased rate of decline in kidney function associated with increases in blood pressure. More specifically, FIG. 9 plots regression line 800 showing that as systolic blood pressure (SBP) increases, a patient's glomerular filtration rate reduces at a higher rate.

Referring to FIG. 9, the present inventors have discovered that therapeutic renal denervation also resulted in a renoprotective benefit beyond that which is accountable for by the decrease in blood pressure. Reference points 802 indicate previous individual studies that have measured the relationship between blood pressure and rate of GFR decline. In the present study, a treatment group of 42 patients with declining kidney function and an average systolic blood pressure of 177 mm Hg were treated with renal denervation. The regression line 800 predicted for this patient group a substantial rate of GFR decline (about −12 mL/min annually), as indicated by reference point 804 at the lower right portion of the graph. To put this in context, a patient with mild chronic kidney disease (Stage 2) and also having the group's average systolic blood pressure of 177 mm Hg would likely be in kidney failure (Stage 5) within a few years.

The treatment group exhibited a 26 mm Hg reduction in systolic blood pressure twelve months following renal denervation. Based on regression line 800, this average reduction in blood pressure was expected to have reduced the average decline in kidney function from about −12 mL/min to about −8 mL/min. However, as shown by line 810, the patients exhibited an average reduction in GFR of about −2.7 mL/min, which represents a substantial improvement in kidney function. This improvement was well beyond what was to be expected based solely on the change in blood pressure.

This somewhat surprising renoprotective benefit can be partially explained by the effect of renal denervation on the RAAS system. In particular, norepinepherine spillover studies have shown that blood renin levels are approximately halved after renal denervation. This can be thought of as a result of the direct reduction of efferent nerve activity, which influences activation of the RAAS system. Use of anti-hypertensive pharmaceuticals such as ACE inhibitors can sometimes present a similar benefit due to their impact on the RAAS system. The cause of this renoprotective effect is not well understood but is thought to be related to metabolic changes in the RAAS induced by the ACE inhibitors direct effect on this hormonal system.

Figure 10A:
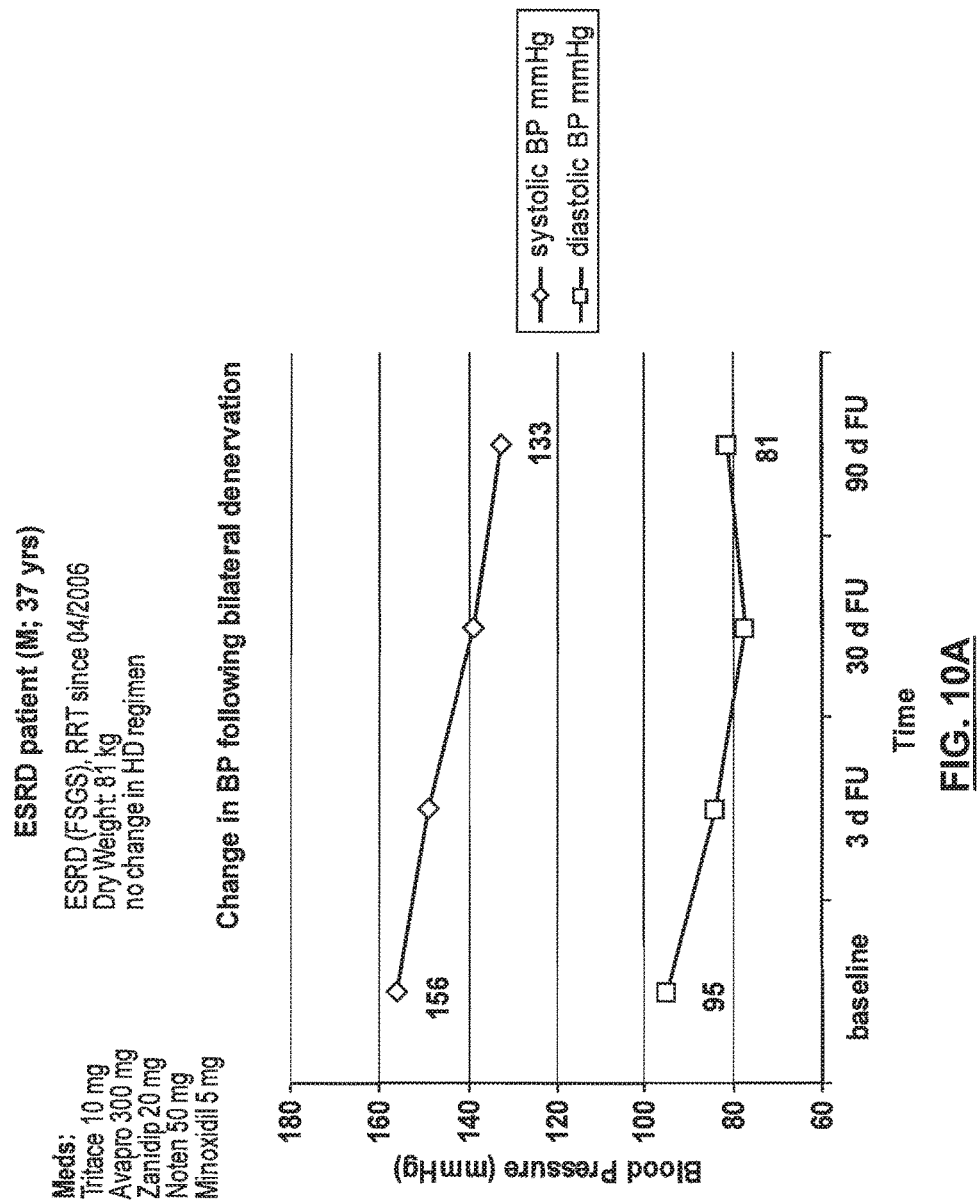
FIG. 10A is a graph illustrating changes in blood pressure for a patient who underwent therapeutic renal neuromodulation.

Additional results from an ESRD patient show improvements in blood pressure and other physiological parameters after renal denervation. In particular, a 37-year-old male with ESRD due to focal segmental glomerulosclerosis underwent bilateral renal denervation. The patient was on renal replacement therapy in addition to 5 anti-hypertension drugs. FIG. 10A shows a decrease in systolic and diastolic blood pressure for the patient at 3 months post-treatment. FIG. 10B-10D show MSNA for the same patient at baseline (FIG. 10B), 3 months (FIG. 10C), and 12 months (FIG. 10D) post-treatment.

D. Therapeutic Renal Neuromodulation in the Treatment of Insulin Resistance, Diabetes, and Metabolic Syndrome The present inventors have also further discovered that therapeutic renal neuromodulation may have a positive impact on the progression of insulin resistance and diabetes. The following provides a brief overview of the physiology associated with insulin resistance, and the results of a study conducted on several patients after undergoing renal neuromodulation showing significant improvements in insulin resistance and diabetic control.

The simplest method to measure insulin resistance is by measuring blood glucose and blood insulin levels after an overnight fast. C-peptide, a byproduct of insulin production, is also measured as an indicator of insulin synthesis. Patients with more insulin resistance tend to have higher insulin levels even at normal fasting glucose levels. The homeostasis model assessment (HOMA) index was developed to linearly correlate with the level of insulin resistance. It is defined as the product of the fasting glucose and fasting insulin levels multiplied by a normalization constant. Patients with normal insulin sensitivity have a HOMA level of 1. Because the HOMA index is measured at a static timepoint when the patient is fasting, it reflects insulin sensitivity but provides little information about the rate of insulin secretion in response to a glucose load. Such a situation is more similar to physiologic normal insulin secretion.

Insulin secretion in response to a glucose load is typically measured using the oral glucose tolerance test (OGTT). In this test, the patient drinks a sugary glucose solution and blood insulin and glucose levels are monitored over 2 hours. Normal patients are able to efficiently store blood glucose, while patients with diabetes or the metabolic syndrome commonly continue to have high blood glucose levels 2 hours after the glucose load. Using the data from the OGTT, the level of insulin resistance can be estimated.

Figure 11:
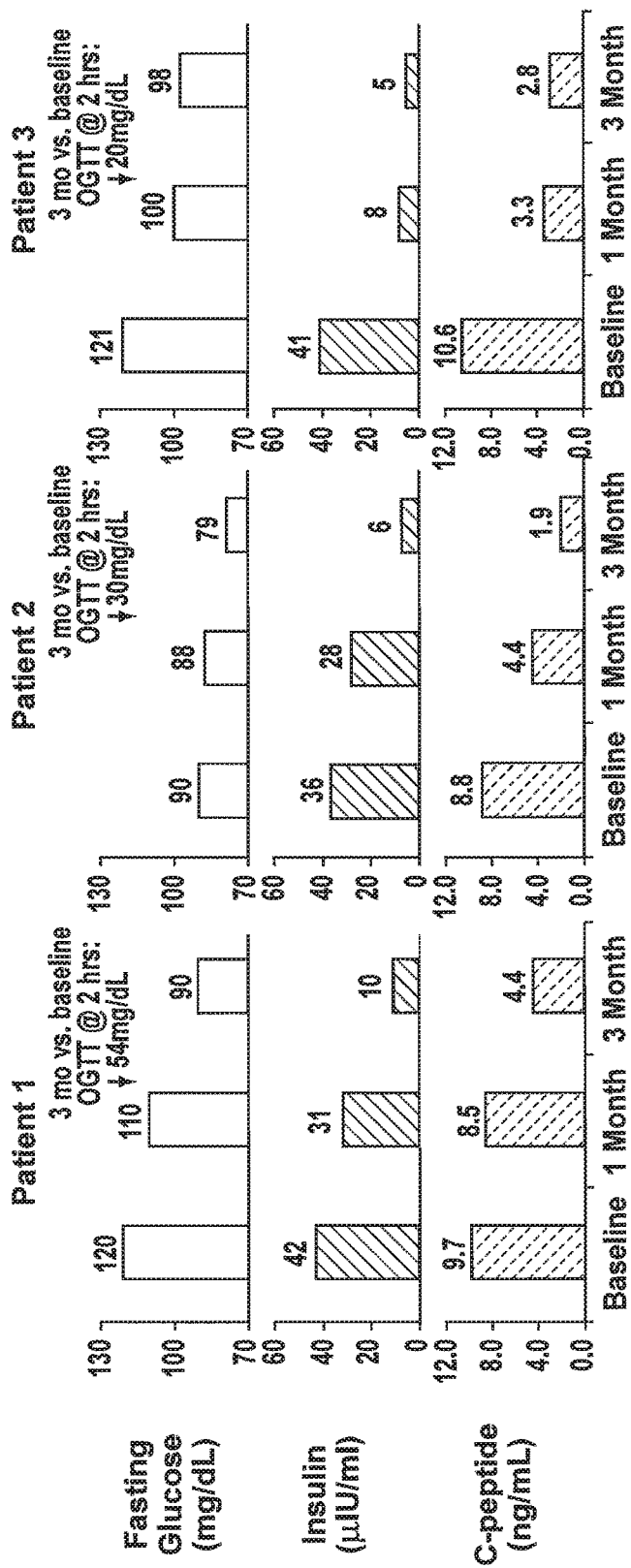
FIG. 11 is a diagram illustrating changes in fasting glucose, insulin, and C-peptide for selected patients after undergoing therapeutic renal neuromodulation.

Referring to FIG. 11, in one particular example it has been shown that therapeutic renal neuromodulation in three pre-diabetic patients caused the levels of fasting blood glucose to fall from the pre-diabetic range (i.e., 100-125 mg/dl) back into the normal range (i.e., 70-100 mg/dl). As further shown in FIG. 11, insulin and C-peptide levels for the three patients also fell at least 50% three months after the renal denervation procedure. These results suggest improved insulin sensitivity. In addition, the patients' blood glucose levels measured two hours after OGTT fell about 20-54 mg/d, indicating reduced glucose tolerance.

Diabetes control is typically quantified by measurement of HgA1c, a form of the protein hemoglobin to which glucose molecules are chemically attached. Hemoglobin is a ubiquitous protein found in the bloodstream. Exposure to elevated levels of glucose (such as is typically found in diabetes patients) results in a chemical reaction where the glucose molecules attach to the hemoglobin. Levels of HgA1c represent a patient's glucose control over the last 2-3 months. Levels above 7%, for example, indicate poorly controlled diabetes. Patients who take metformin, a common anti-diabetic medication, to control their diabetes are typically able to decrease their HgA1c level by about 1%.

Figure 12:
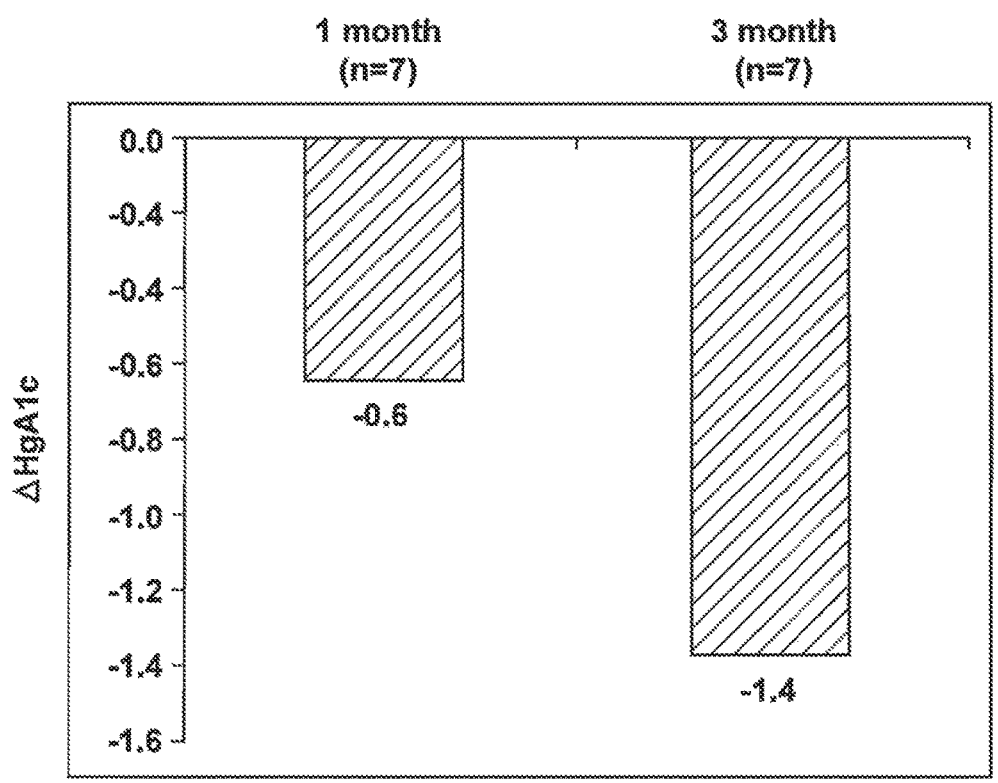
FIG. 12 is a diagram illustrating changes in HgA1c in a number of diabetic patients after undergoing therapeutic renal neuromodulation.

As shown in FIG. 12, however, patients who underwent therapeutic renal neuromodulation presented significant reductions in levels of HgA1c. In particular, FIG. 12 illustrates data from seven diabetic patients with baseline HgA1c greater than 6%. After undergoing renal denervation, the patients experienced a 0.6% decrease in HgA1c one month after the procedure, followed by a 1.4% decrease in HgA1c three months after the procedure.

The studies disclosed herein indicate that renal neuromodulation or denervation is expected to improve insulin resistance and diabetic control, and limit the long term progression of diabetes. A comparable improvement in HgA1c is not typically observed with anti-hypertensive medications, including sympatholytics such as moxonidine. Reduction in HgA1c is correlated with reduced progression of diabetes and the metabolic syndrome. Lower HgA1c levels are also directly associated with reduced risk of kidney failure and cardiovascular events and death.

Figure 13:
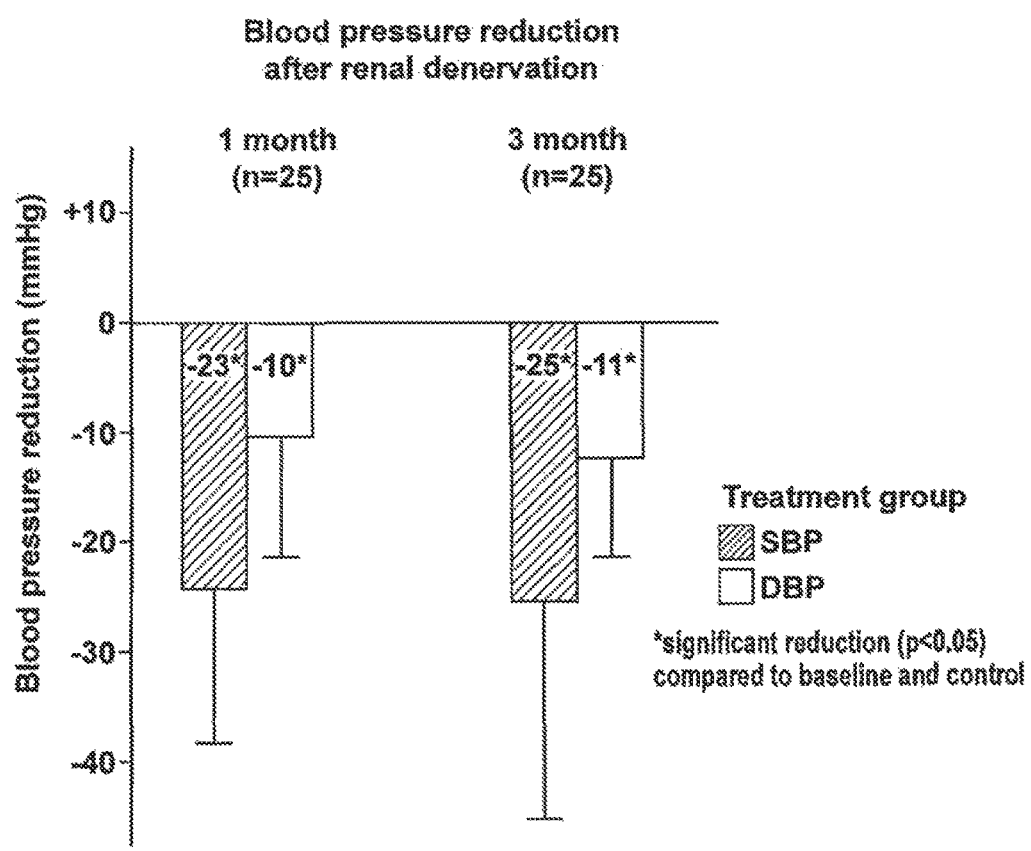
FIG. 13 is a graph illustrating changes in blood pressure for patients who underwent therapeutic renal neuromodulation versus a control group.
Figure 14:
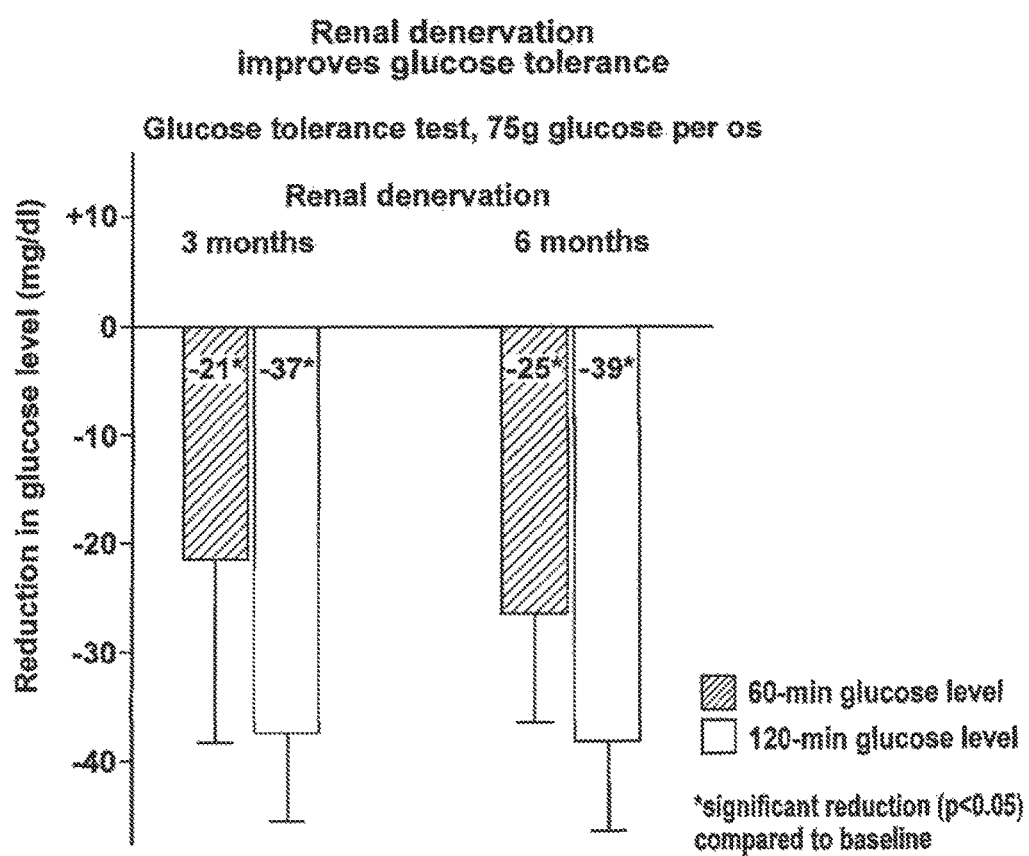
FIG. 14 is a diagram illustrating change in glucose tolerance for the patients and control group of FIG. 13.

FIGS. 13 and 14 and Tables 1-3 show results from a 36 patient study, including 25 patients who underwent therapeutic renal denervation and 11 control patients. These patients were followed at 1, 3, and 6 months after the procedure for indicators related to diabetes, insulin resistance and impaired glucose tolerance. In particular, patients selected for the study had office blood pressure 160 mmHg despite anti-hypertensive medications and eGFR (MDRD formula) mL/min/1.73 m². Key exclusion criteria were known secondary cause of hypertension, Type I diabetes mellitus or renovascular abnormalities, e.g., significant renal artery stenosis, prior renal stenting or angioplasty, dual renal arteries. Patient characteristics were as follows: n=36 (11 control), age 56.9±10 years, 5.6±1.4 antihypertensive medications, RR 178/94±16/13 mmHg, HR 71±14 bpm, BMI 31.4±5.5 kg/m$^2$, Type 2 diabetes on medication, n=15. Renal denervation was performed via catheter-based RF ablation in the renal artery. Median procedure time was 46 minutes and the procedure included 6 RF ablations of up to 2 minutes/ablation at 8 W. No detectable vascular complications were found after 3 and 6 months post-procedure. Of the patients in the treatment group 0 of 25 (0%) exhibited a progression of diabetic status (i.e. either progression from glucose intolerance to diabetic or from normal to glucose intolerant), while 2 of 11 (18%) patients in the control group demonstrated a progression of diabetic status in 6 months. Conversely, 4 of 25 (16%) of patients in the treatment group exhibited a reversal of diabetic status (i.e. from glucose intolerant to normal, or from diabetic to glucose intolerant) while 0 of 11 (0%) of the control group demonstrated a reversal.

TABLE 1

Blood pressure reduction after renal denervation.

| Treatment group | SBP (mmHg) | DBP (mmHg) |
|---|---|---|
| Baseline (25) | 180 ± 14 | 97 ± 5 |
| 1 month (25) | 157 ± 14* | 87 ± 11* |
| 3 months (25) | 155 ± 20* | 86 ± 11* |

*significant reduction (p < 0.05) compared to baseline

TABLE 2

Renal denervation reduces fasting glucose.

| | Treatment group Glucose (mg/dl) | Control group Glucose (mg/dl) |
|---|---|---|
| Baseline (25/11) | 118 ± 20 | 120 ± 22 |
| 1 month (25/11) | 110 ± 14* | 132 ± 43 |
| 3 months (25/11) | 106 ± 12* | 121 ± 21 |
| 6 months (25/11) | 105 ± 18* | 119 ± 25 |

*significant reduction (p < 0.05) compared to baseline

TABLE 3

Renal denervation improves glucose metabolism

| Treatment group | Glucose (mg/dl) | Insulin (mU/l) | C-peptide (µg/l) | HOMA-IR |
|---|---|---|---|---|
| Baseline (25) | 118 ± 20 | 20.7 ± 11.8 | 6.1 ± 3.6 | 6.1 ± 4.3 |
| 1 month (25) | 110 ± 14* | 12.9 ± 7.3* | 3.3 ± 1.5* | 3.5 ± 1.8* |
| 3 months (25) | 106 ± 12* | 11.1 ± 4.8* | 3.1 ± 1.1* | 2.9 ± 1.3* |
| 6 months (25) | 105 ± 18* | 10.5 ± 4.6 | 3.2 ± 1.1 | 2.7 ± 1.4 |

*significant reduction (p < 0.05) compared to baseline
HOmeostasisModelAssessment-InsulinResistance (HOMA-IR) = (FPI × FPG)/405

Figure 15:
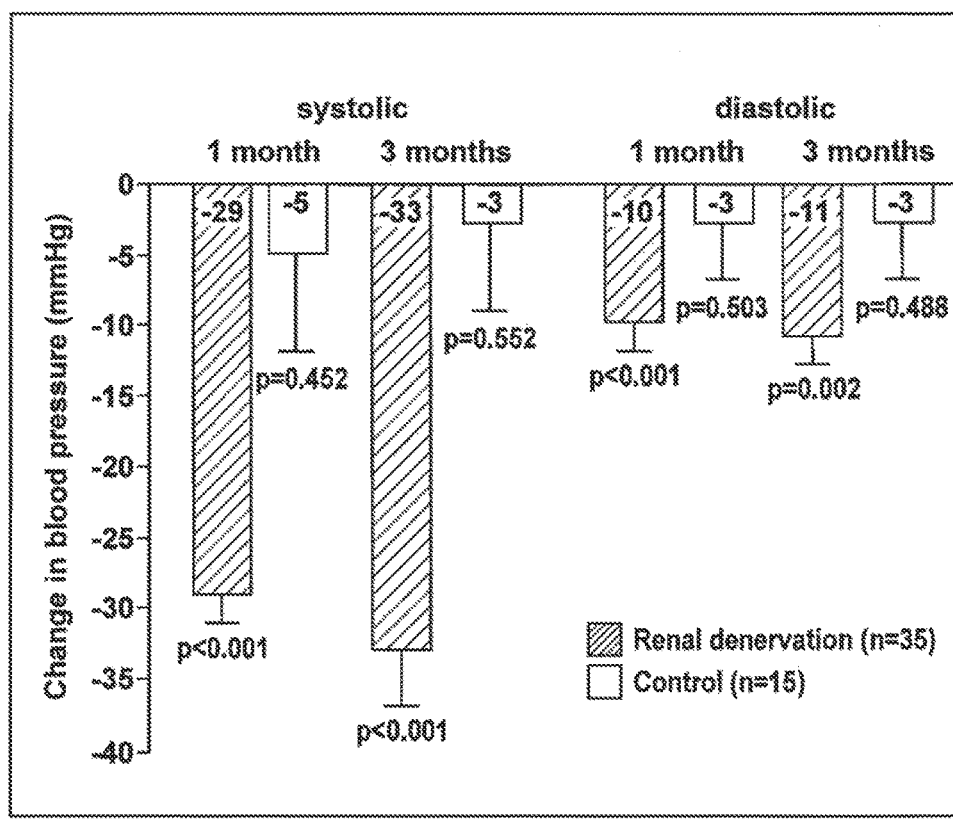
FIG. 15 is a graph illustrating changes in blood pressure for patients who underwent therapeutic renal neuromodulation versus a control group.
Figure 17:
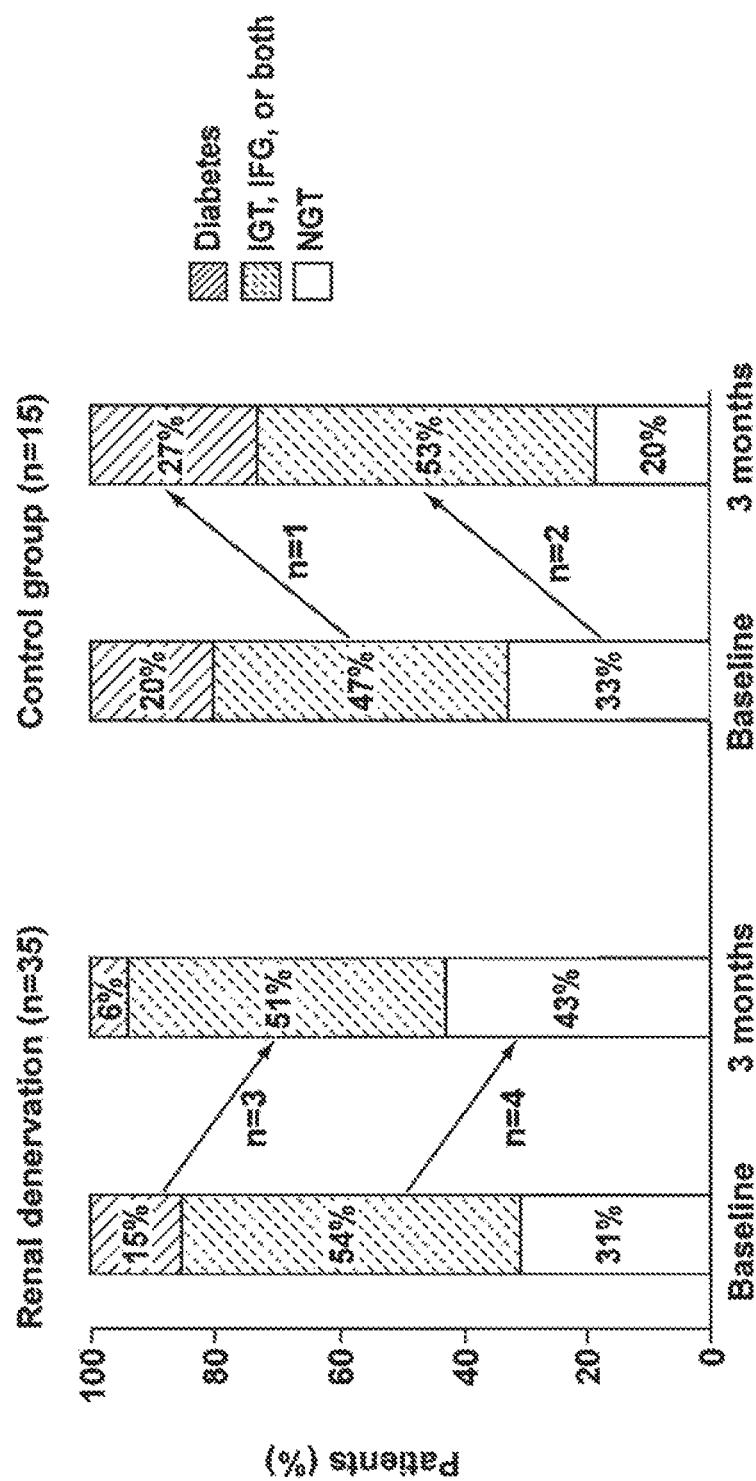
FIG. 17 shows changes in clinical designation for the patients and control group of FIG. 15.

FIGS. 15-17 and Tables 4-5 show results from a study of 50 patients with therapy-resistant hypertension. The study investigated the effect of catheter-based renal sympathetic denervation on glucose metabolism and blood pressure control in patients with drug-resistant hypertension.

Eligible patients were older than 18 years and had an office blood pressure of 160 mmHg (150 mmHg for type 2 diabetics) or more, despite being treated with at least 3 antihypertensive drugs (including one diuretic), with no changes in medication for a minimum of 2 weeks prior to enrolment. Patients were included if they were not pregnant and had a glomerular filtration rate 45 mL/min/1.73 m$^2$ (using the MDRD formula). Patients with renal artery anatomy ineligible for treatment (main renal arteries <4 mm in diameter or <20 mm in length, haemodynamically or anatomically significant renal artery, abnormality or stenosis in either renal artery, a history of prior renal artery intervention including balloon angioplasty or stenting, multiple main renal arteries in either kidney), type 1 diabetes, myocardial infarction, unstable angina pectoris, cerebrovascular accident within the last 6 months, or haemodynamically significant valvular disease were excluded from the study.

Renal angiograms were performed via femoral access to confirm anatomic eligibility. The treatment catheter (Symplicity® by Ardian, Mountain View, Calif., USA) was introduced into each renal artery using a guiding catheter. Up to 6 ablations at 8 watts for 2 minutes each were performed in both renal arteries. Treatments were delivered from the first distal main renal artery bifurcation to the ostium proximally and were spaced longitudinally and rotationally under fluoroscopic guidance. Catheter tip impedance and temperature were constantly monitored, and radio frequency energy delivery was regulated according to a predetermined algorithm. All patients underwent a complete history and physical examination, assessment of vital signs, review of medication, blood chemistries (including serum creatinine), as well as fasting glucose, insulin, C-peptide, and HbA1c at baseline and at each follow-up visit, performed at 1 and 3 months. An OGTT was performed at baseline and after 3 months. The patients were instructed to fast for at least 8-12 hours prior to the OGTT and blood sampling. The OGTT consisted of fasting, 60-, and 120-min glucose measures. Plasma glucose concentration was assessed using the glucose-oxidase method. Plasma insulin and C-peptide concentrations were measured by a chemiluminescent assay. HbA1c was determined using a high-performance liquid chromatography method. The glucose values are expressed in milligrams per deciliter, insulin as international microunits per milliliter, C-peptide as nanograms per milliliter, and HbA1c as %. The insulin sensitivity index was calculated from fasting glucose and insulin values as described: HOMA-IR=(FPG×FPI)/405. FPG and FPI are fasting glucose plasma glucose and fasting plasma insulin, respectively. The Quantitative Insulin Sensitivity Check Index ($IS_{QUICKI}$) was calculated by: $IS_{QUICKI}=1/[\log(FPI)+\log(FPG)]$. Patients were interviewed as to whether they had taken their complete medication. Office blood pressure readings were taken in a seated position after 5 minutes of rest according to the standard joint national committee VII guidelines. Averages of the triplicate measures were used. Physicians were instructed not to change medications except when medically required. Patients were instructed to remain adherent to their prescribed drugs and defined doses at each visit.

Changes in fasting, 60-min and 120-min glucose as well as insulin, C-peptide, HbA1c, HOMA-IR, $IS_{QUICKI}$ and office blood pressures were analysed from baseline to 1 and 3 months by repeated measures analysis of variance with pair-wise comparison of significant values. A two-tailed p value of less than 0.05 was regarded as statistically significant. Glucose levels during OGTT were analysed with a paired t-test to compare baseline with 3-months results. The Bonferoni correction for multiple comparisons was applied. Simple associations were assessed with Pearson's tests for two independent proportions. Data are presented as mean±standard error of the mean (SEM). All statistical analyses were performed with SPSS statistical software (version 17.0, SPSS Inc., Chicago, Ill., USA).

Fifty patients were enrolled of whom 35 were assigned to treatment group following protocols of ongoing therapeutic renal denervation trials (NCT00664638 and NCT00888433) and 15 patients were assigned to the control group. The treatment and control group were well matched concerning their baseline characteristics (Table 4). All patients were maintained on baseline antihypertensive medication and followed for 3 months. Table 4 shows the demographic indicators and clinical characteristics. Most patients were male (n=34, 68%). The mean age was 59.3±1.4 years. On average, patients were taking 5.5±0.2 antihypertensive drugs with 47 (94%) receiving an angiotensin-converting enzyme inhibitor, angiotensin II receptor blocker, or both, 44 (88%) beta blockers, 36 (72%) calcium-channel blockers, and 34 (68%) centrally acting sympatholytics. All patients received diuretics, with 14 (28%) taking aldosterone antagonists. Patients with type 2 diabetes (n=20, 40%) were diagnosed at least 12 months ago. Diagnosis was confirmed as recommended by the American Diabetes Association. Sixteen patients received antidiabetic drugs: metformin (n=15), gliclazide (n=5) or combined therapy. None of the patients changed the antidiabetic treatment during follow-up.

TABLE 4

Baseline patient characteristics.

|  | All patients (n = 50) | Renal denervation (n = 35) | Control group (n = 15) | p |
|---|---|---|---|---|
| Age | 59.3 ± 1.4 | 57.9 ± 1.6 | 62.7 ± 2.6 | 0.11 |
| Sex (female) | 16 (32%) | 9 (26%) | 7 (47%) | 0.19 |
| Type 2 diabetes mellitus | 20 (40%) | 13 (37%) | 7 (47%) | 0.55 |
| on medication | 16 (32%) | 12 (34%) | 4 (27%) | 0.41 |
| eGFR (ml/min/1.72 m$^2$) | 65.0 ± 4.4 | 68.3 ± 4.6 | 59.5 ± 9.2 | 0.36 |
| Heart rate (bpm) | 71.6 ± 2.0 | 71.1 ± 2.1 | 72.8 ± 4.8 | 0.75 |
| Blood pressure (mmHg) | 179/97 ± 3/2 | 178/97 ± 3/3 | 183/97 ± 6/4 | 0.42 |
| Number of antihypertensive drugs | 5.5 ± 0.2 | 5.9 ± 0.2 | 4.8 ± 0.3 | 0.12 |
| Fasting glucose (mg/dl) | 125 ± 4 | 127 ± 4.5 | 119 ± 5.3 | 0.16 |
| Glucose level 60-min, OGTT (mg/dl) | 218 ± 9 | 226 ± 11 | 197 ± 13 | 0.11 |
| Glucose level 120-min, OGTT (mg/dl) | 178 ± 11 | 184 ± 14 | 170 ± 16 | 0.42 |
| Impaired fasting glycaemia, OGTT (n) | 9 (18%) | 5 (14%) | 4 (27%) | 0.42 |
| Impaired glucose tolerance, OGTT (n) | 17 (34%) | 14 (40%) | 3 (20%) | 0.20 |
| Diabetes mellitus, OGTT (n) | 8 (16%) | 5 (14%) | 3 (20%) | 0.24 |
| HbA1c (%) | 6.0 ± 0.1 | 5.9 ± 0.1 | 6.1 ± 0.3 | 0.41 |
| Insulin (μIU/ml) | 19.0 ± 2.3 | 19.9 ± 2.6 | 17.4 ± 5.0 | 0.33 |
| C-peptide (ng/ml) | 4.5 ± 0.5 | 5.2 ± 0.5 | 4.2 ± 0.4 | 0.10 |
| HOMA-IR | 5.9 ± 0.7 | 6.4 ± 0.9 | 5.2 ± 1.2 | 0.23 |
| IS$_{QUICKI}$ | 0.32 ± 0.01 | 0.31 ± 0.01 | 0.33 ± 0.01 | 0.17 | p for renal denervation vs. control group.
Data are mean ± SEM or number (n, %).
eGFR = estimated glomerular filtration rate.
OGTT = oral glucose tolerance test.
HOMA-IR = Homeostasis model assessment.
IS$_{QUICKI}$ = Quantitative Insulin Sensitivity Check Index.

TABLE 5

Change in blood pressure and glucose metabolism at 1 and 3 months.

|  | Treatment group | | | | Control group | | | |
|---|---|---|---|---|---|---|---|---|
|  | 1 month (n = 35) | p* | 3 months (n = 35) | p** | 1 month (n = 15) | p* | 3 months (n = 15) | p** |
| SBP (mmHg) | −29 ± 2 (−16%) | <0.001 | −33 ± 4 (−18%) | 0.001 | −5 ± 7 (−3%) | 0.452 | −3 ± 6 (−2%) | 0.552 |
| DBP (mmHg) | −10 ± 2 (−10%) | <0.001 | −11 ± 2 (−11%) | 0.002 | −3 ± 4 (−3%) | 0.503 | −3 ± 4 (−3%) | 0.488 |
| HR (bpm) | −3.8 ± 1.5 (−5%) | 0.057 | −3.7 ± 1.6 (5%) | 0.091 | −2.5 ± 4.3 (−3%) | 0.203 | −2.1 ± 4.1 (−3%) | 0.481 |
| Fasting glucose (mg/dl) | −9.7 ± 3.2 (−8%) | 0.007 | −12.0 ± 3.4 (−9%) | 0.004 | +4.6 ± 8.2 (+4%) | 0.589 | +5.1 ± 4.3 (+4%) | 0.177 |
| HbA1c (%) | −0.1 ± 0.1 (−2%) | 0.185 | −0.1 ± 0.3 (−2%) | 0.721 | +0.1 ± 0.1 (+2%) | 0.627 | +0.1 ± 0.1 (+2%) | 0.539 |
| Insulin (μIU/ml) | −8.7 ± 3.0 (−44%) | 0.042 | −9.2 ± 3.3 (−46%) | 0.003 | +7.9 ± 7.7 (+45%) | 0.343 | +1.1 ± 2.1 (+6%) | 0.927 |

TABLE 5-continued

Change in blood pressure and glucose metabolism at 1 and 3 months.

| | Treatment group | | | | Control group | | | |
|---|---|---|---|---|---|---|---|---|
| | 1 month (n = 35) | p* | 3 months (n = 35) | p** | 1 month (n = 15) | p* | 3 months (n = 15) | p** |
| C-peptide (ng/ml) | −2.2 ± 0.8 (−49%) | 0.022 | −2.4 ± 0.7 (−46%) | 0.005 | +1.1 ± 0.9 (+27%) | 0.356 | +0.2 ± 0.5 (+5%) | 0.815 |
| HOMA-IR | −3.0 ± 1.1 (−47%) | 0.023 | −3.1 ± 0.9 (−48%) | 0.001 | +2.1 ± 1.7 (+40%) | 0.246 | +0.3 ± 0.6 (6%) | 0.962 |
| IS$_{QUICKI}$ | +0.02 ± 0.01 (+6%) | 0.034 | +0.04 ± 0.01 (+13%) | 0.006 | +0.01 ± 0.02 (+3%) | 0.811 | +0.01 ± 0.06 (+3%) | 0.916 |
| Glucose level 60-min, OGTT (mg/dl) | — | — | −18 ± 12 (−8%) | 0.052 | — | — | +9.7 ± 13 (+5%) | 0.474 |
| Glucose level 120-min, OGTT (mg/dl) | — | — | −27 ± 11 (−15%) | 0.029 | — | — | +15.3 ± 9 (+9%) | 0.124 |
| Impaired fasting glycaemia, OGTT (n) | — | — | −1 | — | — | — | ±0 | — |
| Impaired glucose tolerance, OGTT (n) | — | — | −3 | — | — | — | +2 | — |
| Diabetes mellitus, OGTT (n) | — | — | −3 | — | — | — | +1 | — | p* = 1 month vs. baseline.
p** = 3 months vs baseline.
Data are mean ± SEM and relative changes (%) compared to baseline values or number (n).
SBP: systolic blood pressure.
DBP: diastolic blood pressure.
HR: heart rate.
OGTT: oral glucose tolerance test (performed at baseline and 3 months).
HOMA-IR = Homeostasis model assessment.
IS$_{QUICKI}$ = Quantitative Insulin Sensitivity Check Index.

At baseline, overall mean sitting office systolic blood pressure (SBP) was 179±2.7 mmHg and mean sitting office diastolic blood pressure (DBP) was 97±2.2 mmHg with a heart rate of 71.6±2.0 beats per minute. Renal denervation significantly reduced systolic (−29±2 mmHg, p<0.001) and diastolic blood pressure (−10±2 mmHg, p=0.001) at 1 month after the procedure and persisted to 3 months follow-up (−33/−11±4/2 mmHg, p=0.001/0.002, FIG. 15). Control patients had a slight, but not significant change in blood pressure of −5/−3 mmHg at 1 month (p=0.452/0.503) and −3/−3 mmHg at 3 months (p=0.552/0.488), respectively. Three of the treated patients (9%) were non-responders with a systolic blood pressure reduction of less than 10 mmHg. On average, patients received 5.5 antihypertensive drugs at baseline and were instructed not to change their medications, unless adverse effects occurred. However, in 16 of 50 patients (13 out of the treatment group and 3 out of the control group) a change in antihypertensive medication was necessary after 3 months follow-up. In 13 treated patients antihypertensive medication had to be reduced due to hypotension associated with symptoms. There were no changes in beta blocker or thiazide diuretics. In two control and one treatment patient antihypertensive medication had to be further increased following the development of symptoms or signs felt to be a consequence of hypertension. In order to exclude post-procedural renovascular abnormalities, renal duplex ultrasound was performed at 3 months follow-up and found no detectable abnormalities of the renal arteries. One patient developed a pseudoaneurysm at the femoral access site, which was treated without further sequelae. No other complications were observed.

Three months after denervation, fasting glucose was reduced significantly from 127±4.5 mg/dl to 115±3.8 mg/dl (p=0.004, FIG. 16A) while there were no significant changes in the control group. Insulin levels decreased from 19.9±2.6 µIU/ml to 10.7±3.3 µIU/ml (p=0.003, FIG. 16B), which was associated with a reduction of C-peptide levels from 5.2±0.5 ng/ml to 2.8±0.8 ng/ml (p=0.005, FIG. 16C). At baseline, 11 patients in the treatment group had insulin levels 20 µIU/ml. Treatment decreased this number by 73% (n=8), without changes in the control group. Changes in fasting glucose and insulin levels did not correlate to office systolic (r=0.144, p=0.424 and r=−0.222, p=0.238) or diastolic blood pressure reduction (r=0.05, p=0.805 and r=−0.188, p=0.320). Insulin sensitivity, measured by using HOMA-IR and IS$_{QUICKI}$, increased significantly after renal denervation (FIG. 16D). The HOMA-IR decreased from 6.4±0.9 to 3.3±0.6 (p=0.001) and the IS$_{QUICKI}$ increased from 0.31±0.01 to 0.35±0.01 (p=0.006). HbA1c levels remained nearly at baseline values (5.8±0.2%) and did not change significantly during 3 months of follow-up. Only 4 patients had HbA1c level ≥7.5%. Mean reductions in glucose levels during OGTT after 3 months were −18±12.0 mg/dl (p=0.052) at 60-min and −27±11.2 mg/dl (p=0.029) at 120-min in the treatment group but not in the control group. According to the World Health Organization the results of the OGTT were graded into 3 categories: normal (fasting glucose <110 mg/dl, 120-min glucose <140 mg/dl), impaired fasting glycaemia (fasting glucose ≥110 mg/dl, 120-min glucose <140 mg/dl), impaired glucose tolerance (fasting glucose <126 mg/dl, 120-min glucose ≥140 mg/dl), and diabetes mellitus (fasting glucose ≥126 mg/dl, 120-min glucose ≥200 mg/dl). In 34 patients (treatment group: n=24, control group: n=10) the OGTT at baseline revealed pathological glucose metabolism, divided into 9 patients with impaired fasting glycaemia (IFG), 17 patients with impaired glucose tolerance (IGT), and 8 patients with diabetes mellitus (DM). After the procedure, 7 of 24 patients improved their glucose metabolism during OGTT: IFG, IGT or both regressed by 17% (n=4), DM regressed by 13% (n=3) and the number of patients with normal glucose tolerance (NGT) increased by 17% (n=4). Patients from the control group had no significant changes in glucose or insulin metabolism during follow-up, despite an increase in IFG, IGT or both by n=2 and an increase in DM by n=1 (Table 5, FIG. 17).

Drug treatment was not changed during the 3 months follow-up period, and drugs were homogeneously distributed among the two groups. During the normal 120-day life span of the red blood cell, glucose molecules react with haemoglobin, forming glycated haemoglobin (HbA1c) and indicating long-term serum glucose regulation. All patients, particularly the diabetics, were adequately controlled with their antidiabetic treatment (mean HbA1c 5.9%). Accordingly, no significant changes in HbA1c levels during follow-up of 3 months were detected, while insulin, C-peptide, fasting glucose and insulin sensitivity were significantly changed by renal denervation.

E. Therapeutic Renal Neuromodulation in the Treatment of Obesity and Sleep Apnea Renal denervation leading to a reduction of central sympathetic drive is believed to counteract some of the deleterious effects of obesity-related increase in central sympathetic drive. It is also believed that renal denervation can improve an individual's ability to process glucose. Such a result could positively impact obesity itself.

Renal denervation may also be a viable treatment option for sleep apnea. Since obstructive sleep apnea is related to obesity, reductions in central sympathetic tone via renal denervation may be able to treat obesity-mediated obstructive sleep apnea as well as the downstream consequences involving the RAAS. Additionally, modulation of the SNS via renal denervation might also modulate aspects of the central nervous system responsible for central sleep apnea.

Provided herein are results from a study of 10 patients, selected from a population of 13 patients, with defined resistant hypertension and taking stable anti-hypertensive medication regimes. Changes in the apnea hypopnea index (AHI) after therapeutic renal denervation were observed, and these findings were associated with changes in ambulatory blood pressure monitoring. Inclusion criteria included: age 18 years, systolic blood pressure of 160 mmHg or greater (an average of 3 office/clinic blood pressure readings), receiving and adhering to full doses of a 3 medication antihypertensive drug regimen for a minimum of two weeks prior to screening, an estimated glomerular filtration rate (eGFR) of ≥45 mL/min, using the MDRD calculation.

All patients in the study underwent simultaneous bilateral renal artery treatment without follow-up angiogram. Baseline measurements consisted of vital signs, physical examination, review of medications, basic blood chemistries (including serum creatinine), ambulatory blood pressure measurements (ABPM), full night attended polysomnography (Phillips-Respironics Inc., Alice 5 System, Murrysville, Pa.). The patients were assessed at a 3-month and 6-month follow-up, which consisted of office blood-pressure measurement, physical examination, surveillance for adverse events, blood chemistries (including serum creatinine), other vital signs, ABPM and full night attended polysomnography.

From the group of 13 patients included in this study, 10 patients were diagnosed with sleep apnea (8 obstructive and 2 mixed obstructive/central, AHI >5 events/hour prior to treatment). These patients completed a 3-month and 6-month follow-up evaluation. All included patients were characterized by normal ejection fraction on echocardiography and no clinical signs and symptoms of heart failure. In all patients, estimated glomerular filtration rate was above 60 ml/min/1.73 m$^2$ at baseline, 3-months, and 6-months after the procedure. Anti-hypertensive medication regimes were not changed during the 6-months of follow-up. The 3 excluded patients all had normal AHI at baseline.

Figure 18:
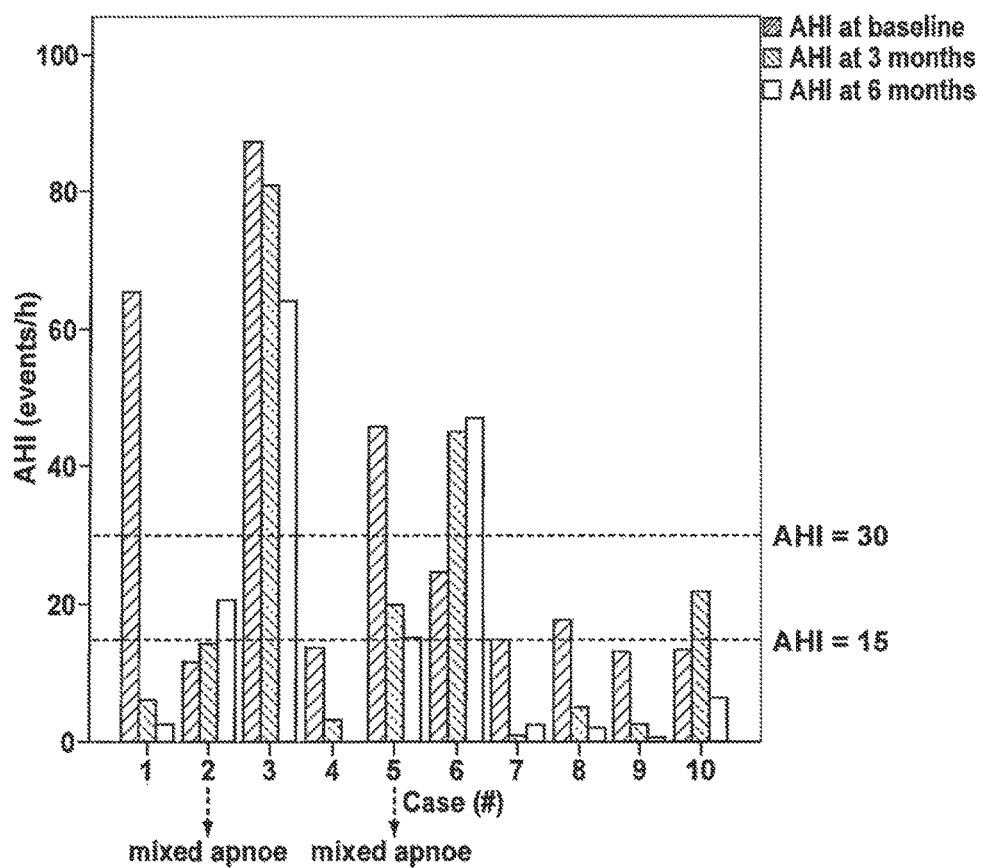
FIG. 18 is a diagram illustrating change in sleep apnea events/hour for 10 patients at baseline, 3 months and 6 months

The mean systolic blood pressure was reduced at 3 months by 22 mm Hg (SD 15) and at 6 months by 32 mm Hg (SD 10) compared to baseline (p<0.01 for 3 and 6 months). The mean diastolic blood pressure was reduced at 3 months by 6 mm Hg (SD 13, p=0.17) and at 6 months by 16 mm Hg (SD 12, p<0.01). As shown in FIG. 18 In 7 of 10 patients an improvement in AHI was observed at 3 months after renal denervation, with an improvement in an additional case at 6 months. It should be noted that in all 3 patients with severe OSA before denervation (2 were receiving CPAP treatment), an improvement in sleep apnea indices was observed. There were 2 patients with mixed (obstructive and central) sleep apnea. In 1 of them a reduction in sleep apnea indices was also observed with a change in AHI −30.5 events/hour at 6 months. Mean AHI at 3 and 6 months after treatment was 20.0 (SD 26.5, p=0.11) events/hour and 16.1 (SD22.2, p=0.059) events/hour compared to 30.7 (SD 26.5) events/hour at baseline. Catheter-based renal sympathetic denervation lowered blood pressure in patients with refractory hypertension and obstructive sleep apnea which was accompanied by improvement of sleep apnea severity. Accordingly, renal sympathetic denervation may be a potentially useful option for patients with refractory hypertension and obstructive sleep apnea.

F. Therapeutic Renal Neuromodulation and Effects on Physiological Parameters

Renal denervation leading to a reduction of central sympathetic drive may improve and/or alter a number of physiological parameters, including sympathetic, metabolic, and renal parameters. FIGS. 19-30 show a variety of physiological parameters for three patients at baseline and 12 weeks post-denervation treatment.

Figure 19:
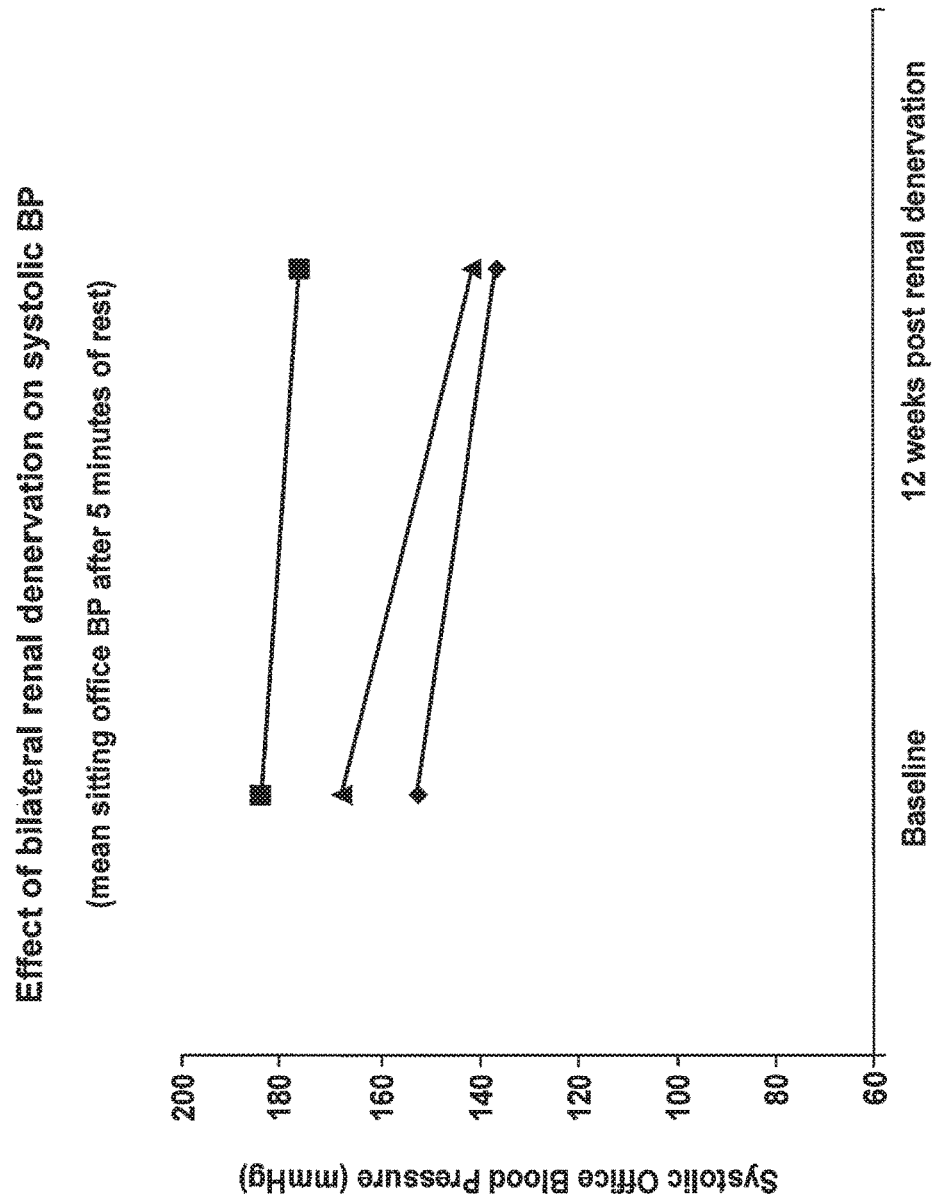
FIG. 19 is a graph showing changes in mean sitting office systolic blood pressure after 5 minutes of rest for patients who underwent therapeutic renal neuromodulation.
Figure 20:
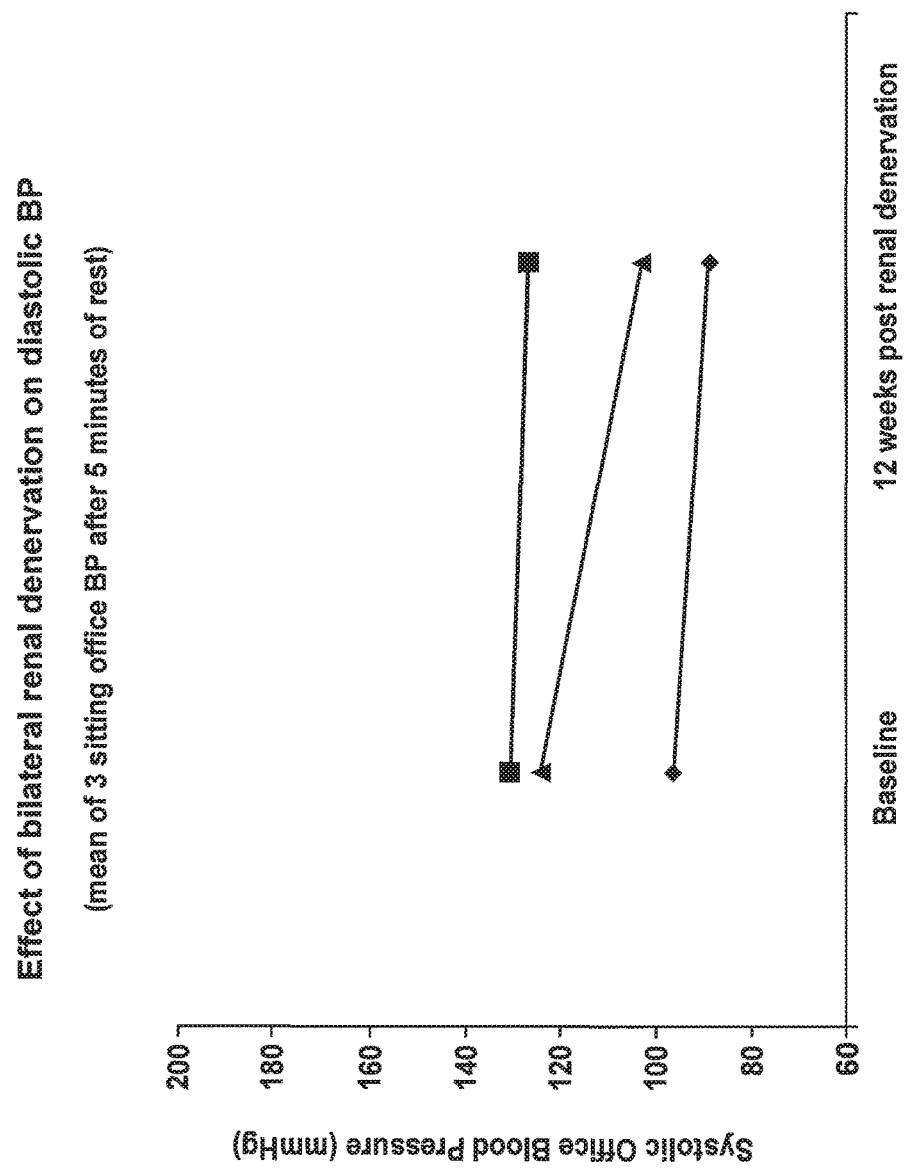
FIG. 20 is a graph showing mean of 3 sitting office diastolic blood pressure measurements after 5 minutes of rest for patients who underwent therapeutic renal neuromodulation.
Figure 21:
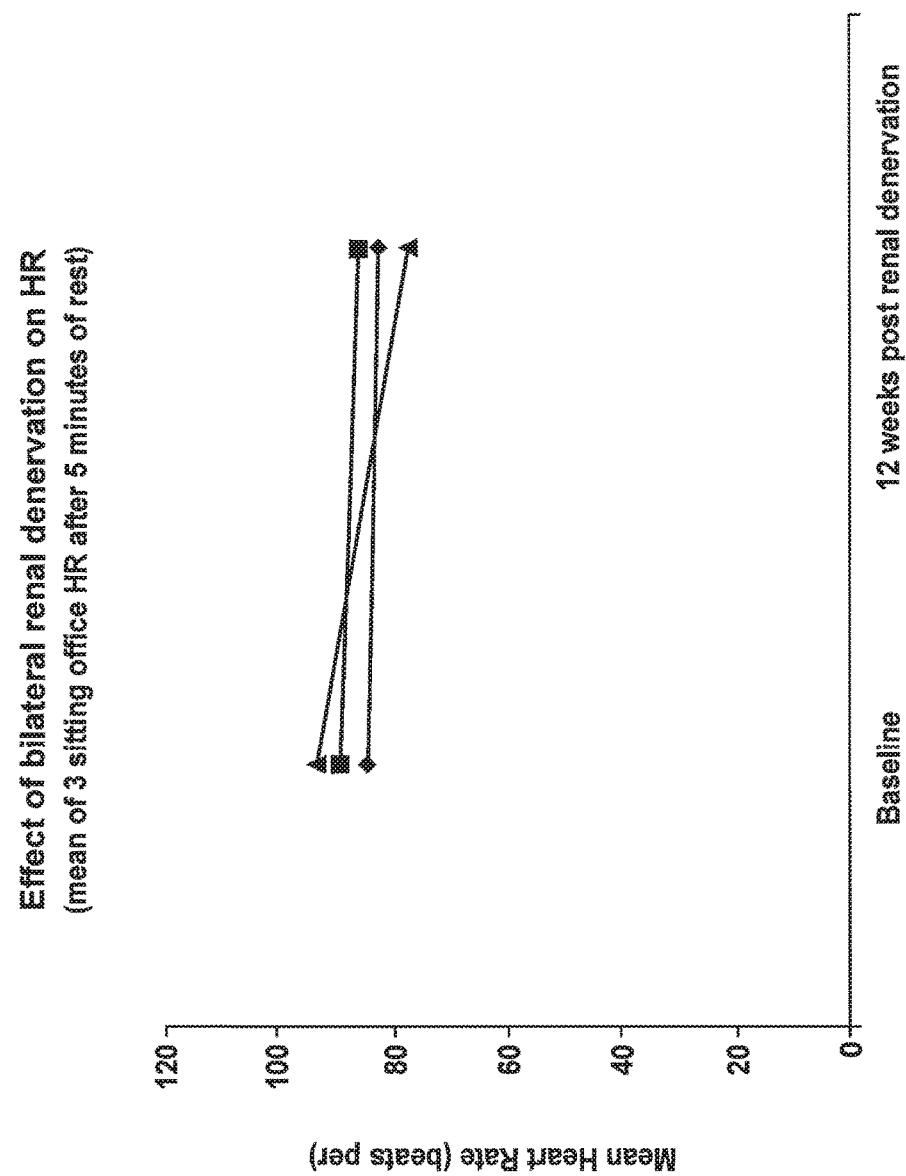
FIG. 21 is a graph showing changes in a mean of 3 sitting office heart rate measurements after 5 minutes of rest for patients who underwent therapeutic renal neuromodulation.
Figure 22:
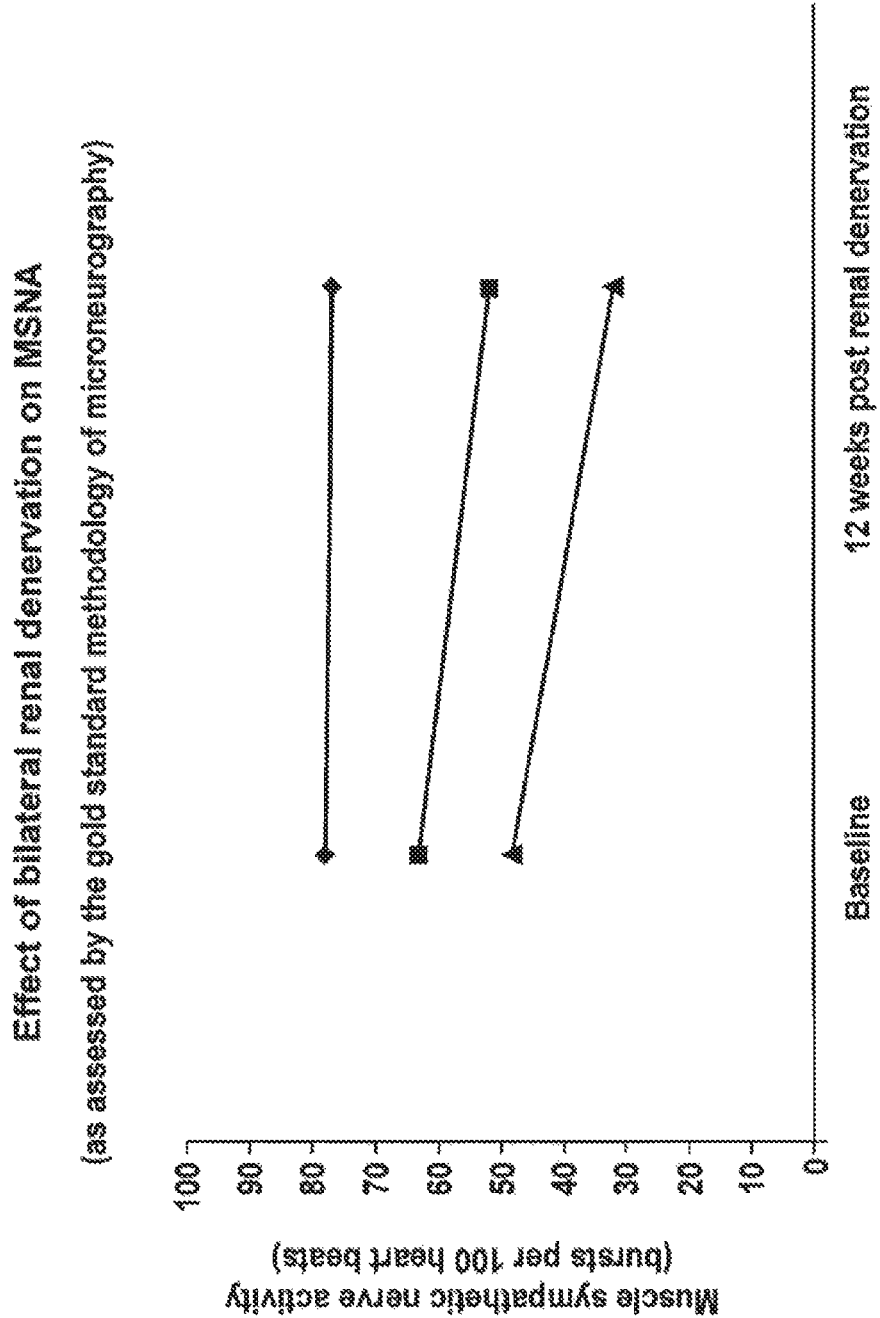
FIG. 22 is a graph showing effects on MSNA as assessed by microneurography for patients who underwent therapeutic renal neuromodulation.
Figure 23:
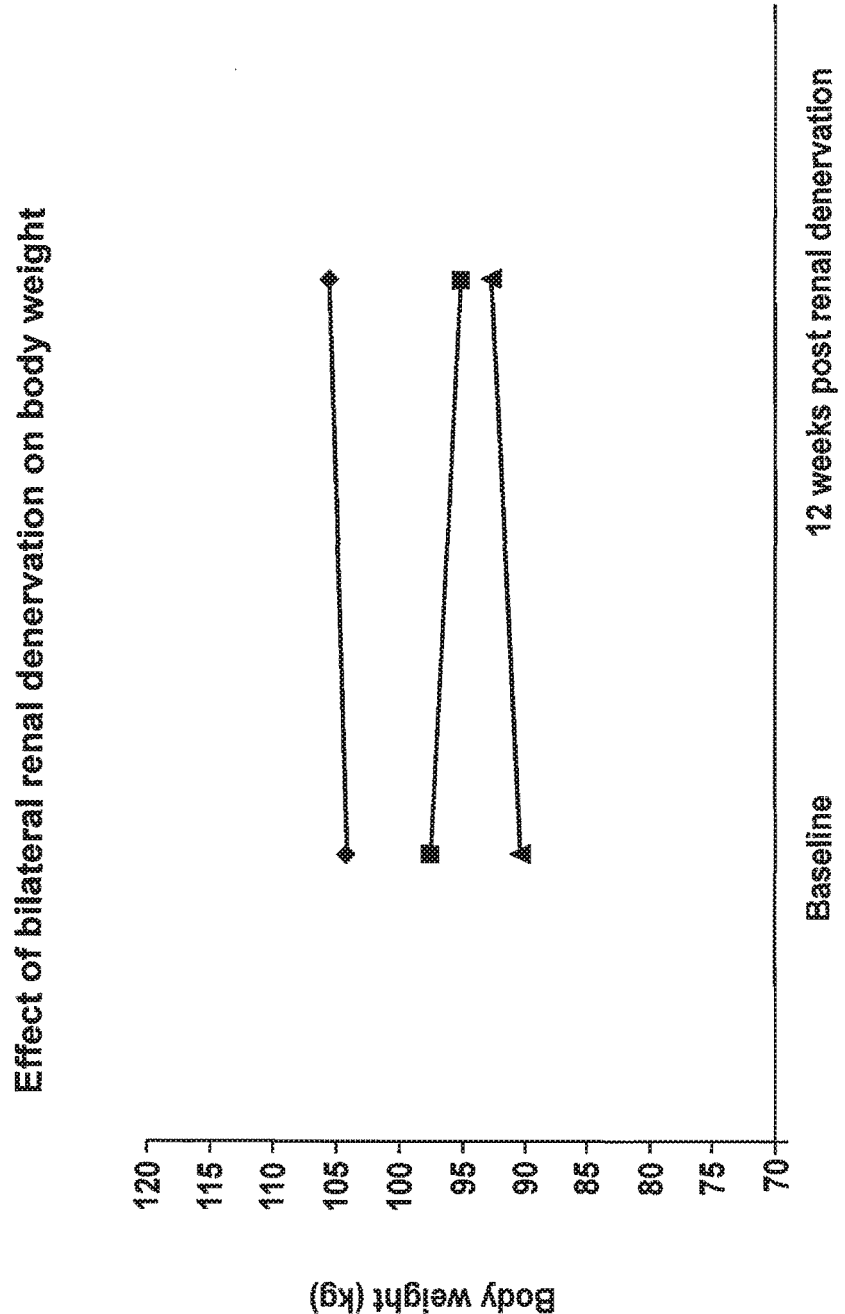
FIG. 23 is a graph showing the effects of bilateral renal denervation on body weight for patients who underwent therapeutic renal neuromodulation.
Figure 24:
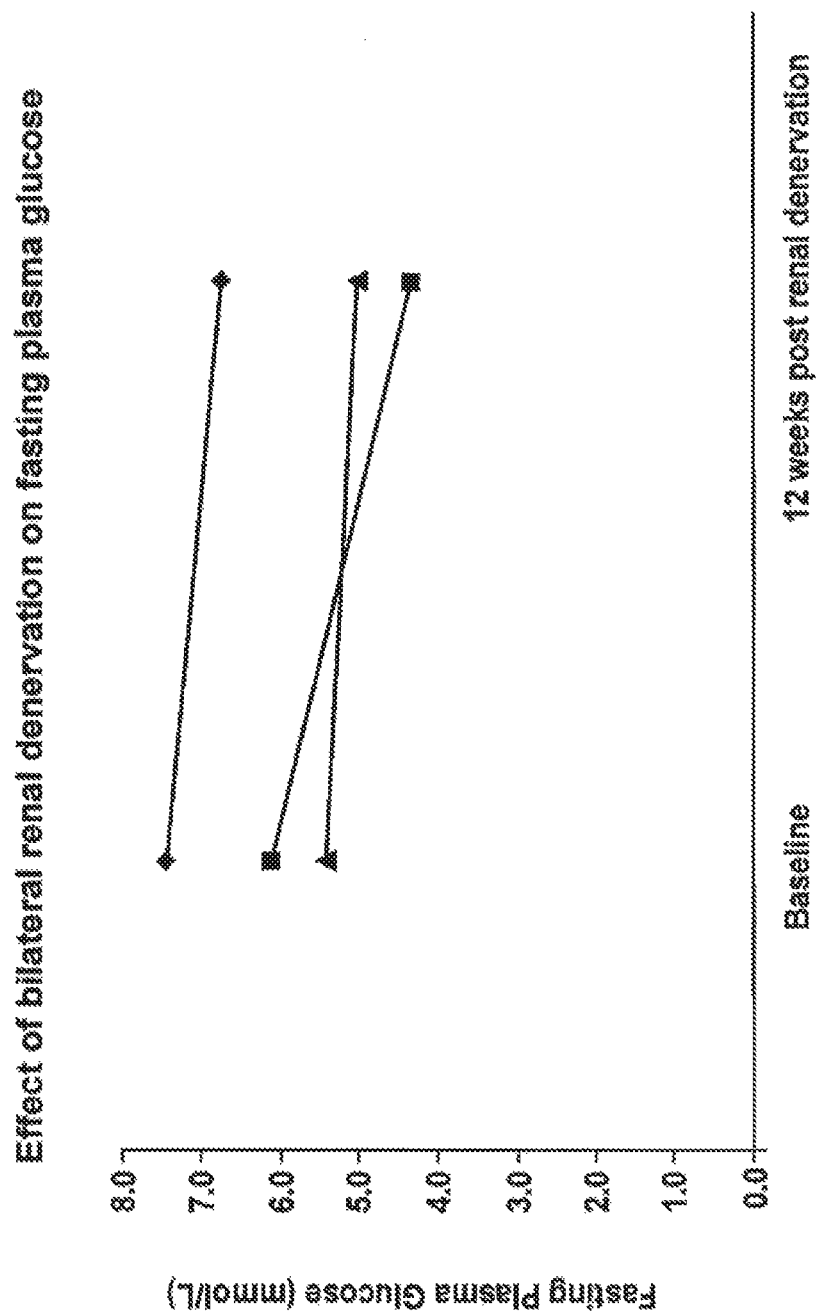
FIG. 24 is a graph showing the effects on fasting plasma glucose for patients who underwent therapeutic renal neuromodulation.
Figure 25:
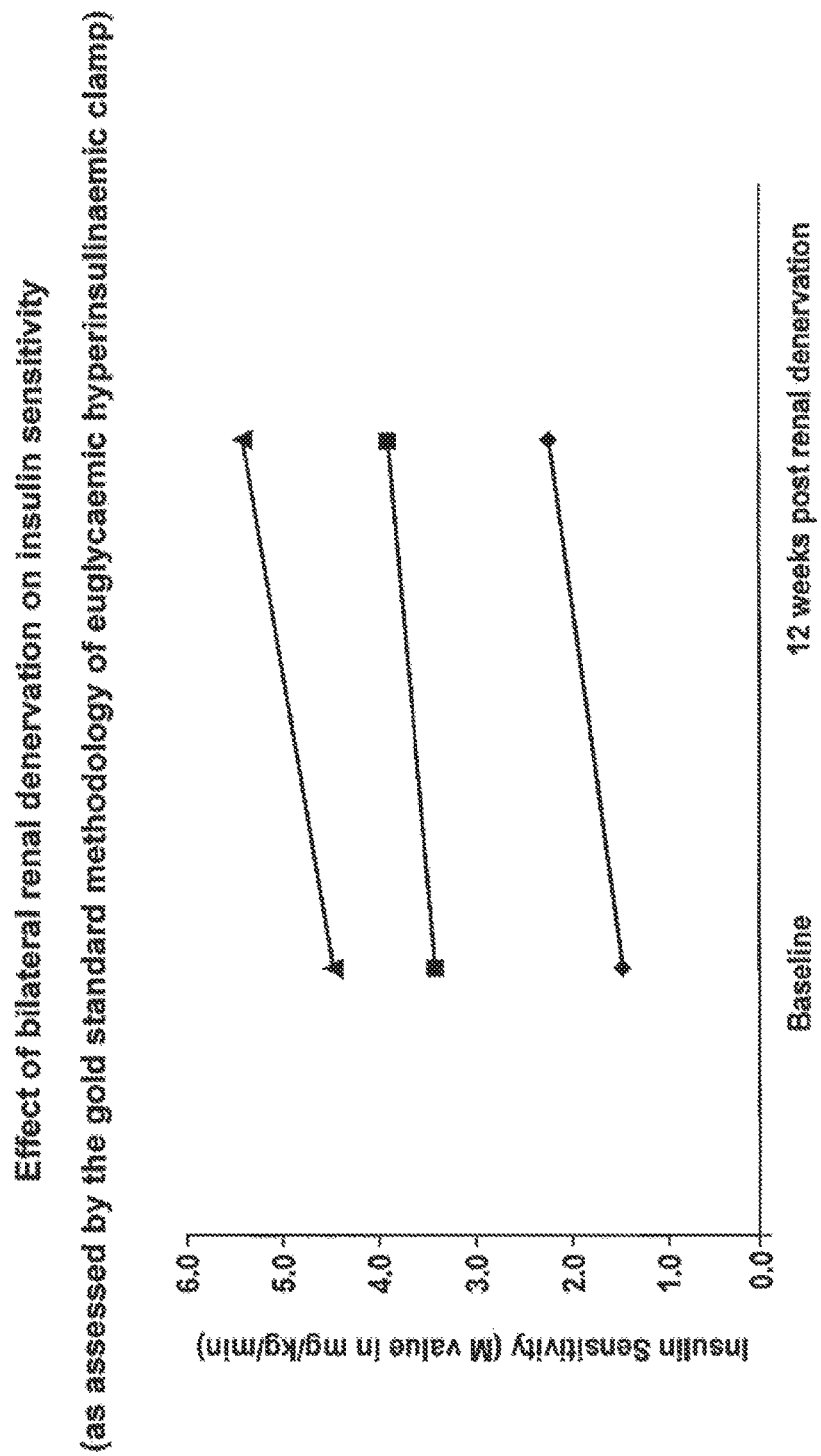
FIG. 25 is a graph of changes in insulin sensitivity for patients who underwent therapeutic renal neuromodulation.
Figure 26:
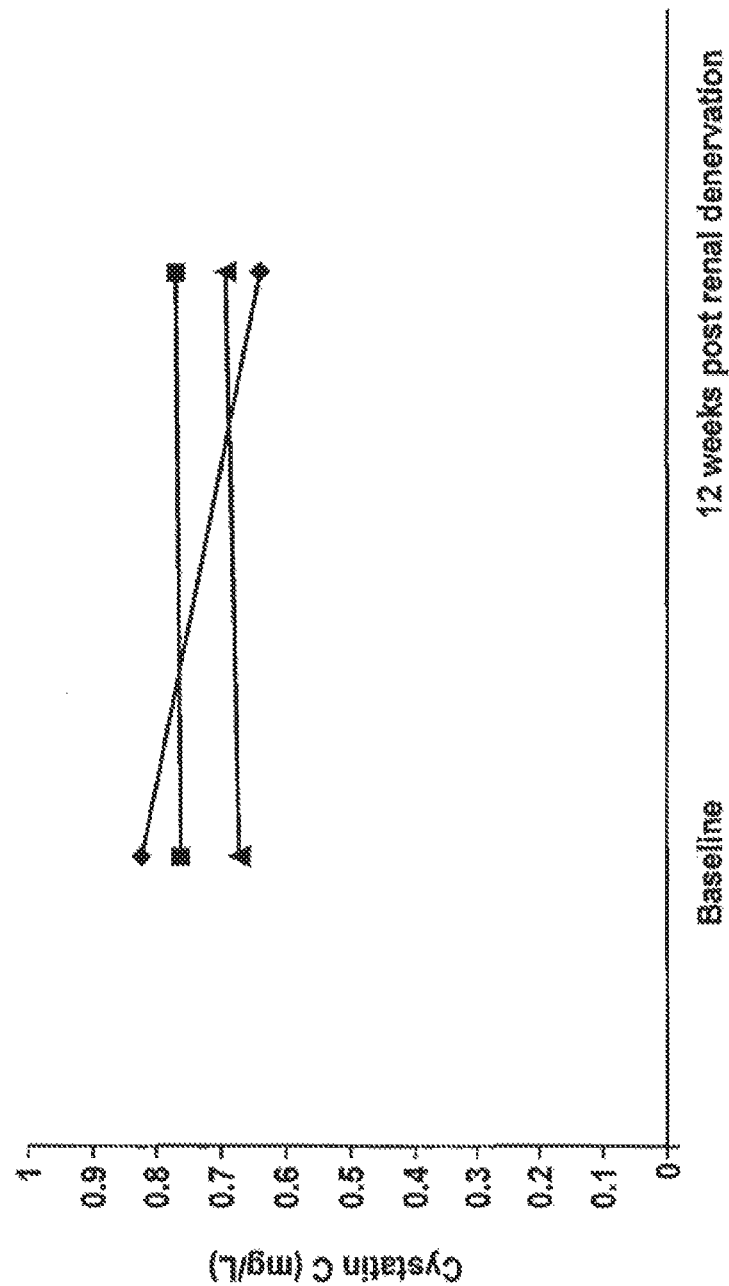
FIG. 26 is a graph of changes in measured cystatin C for patients who underwent therapeutic renal neuromodulation.
Figure 27:
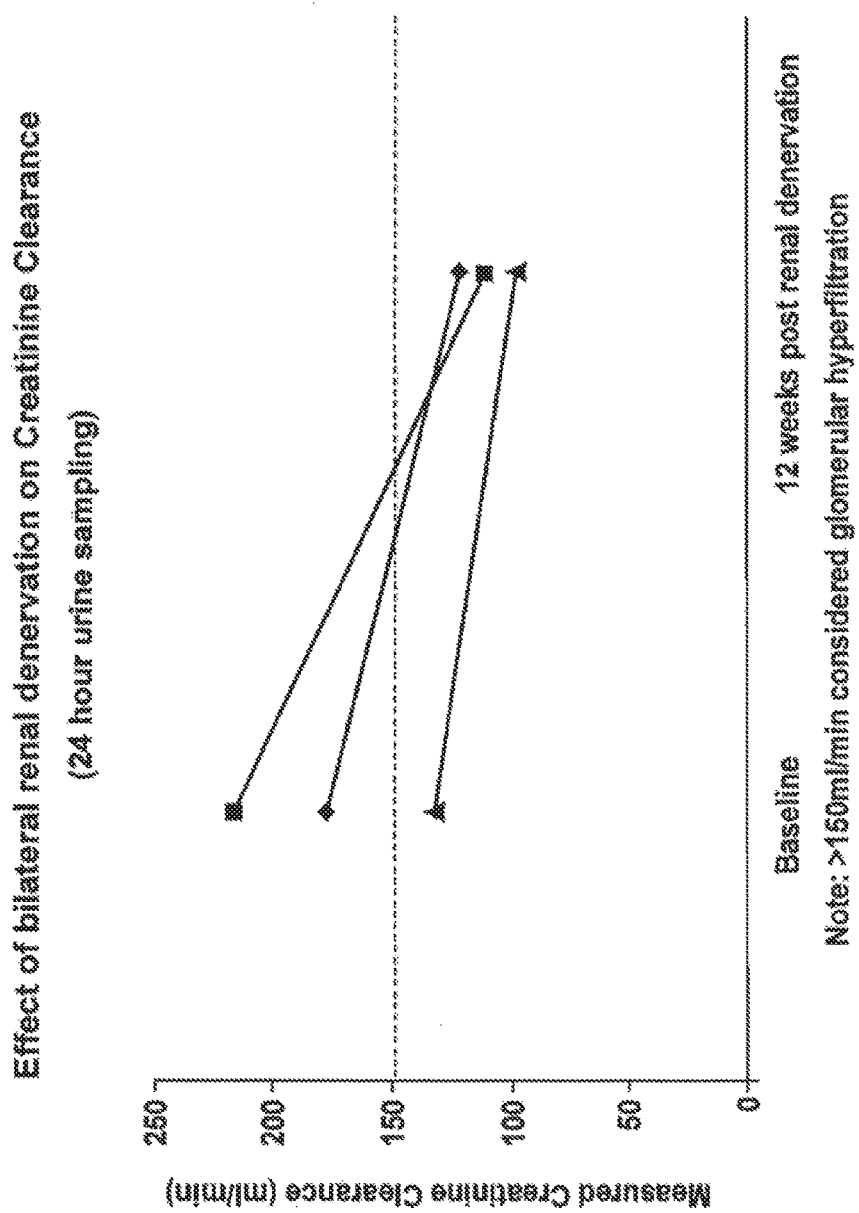
FIG. 27 shows the changes at 12 weeks post-treatment in creatinine clearance over a 24 hour urine sampling for patients who underwent therapeutic renal neuromodulation.
Figure 28:
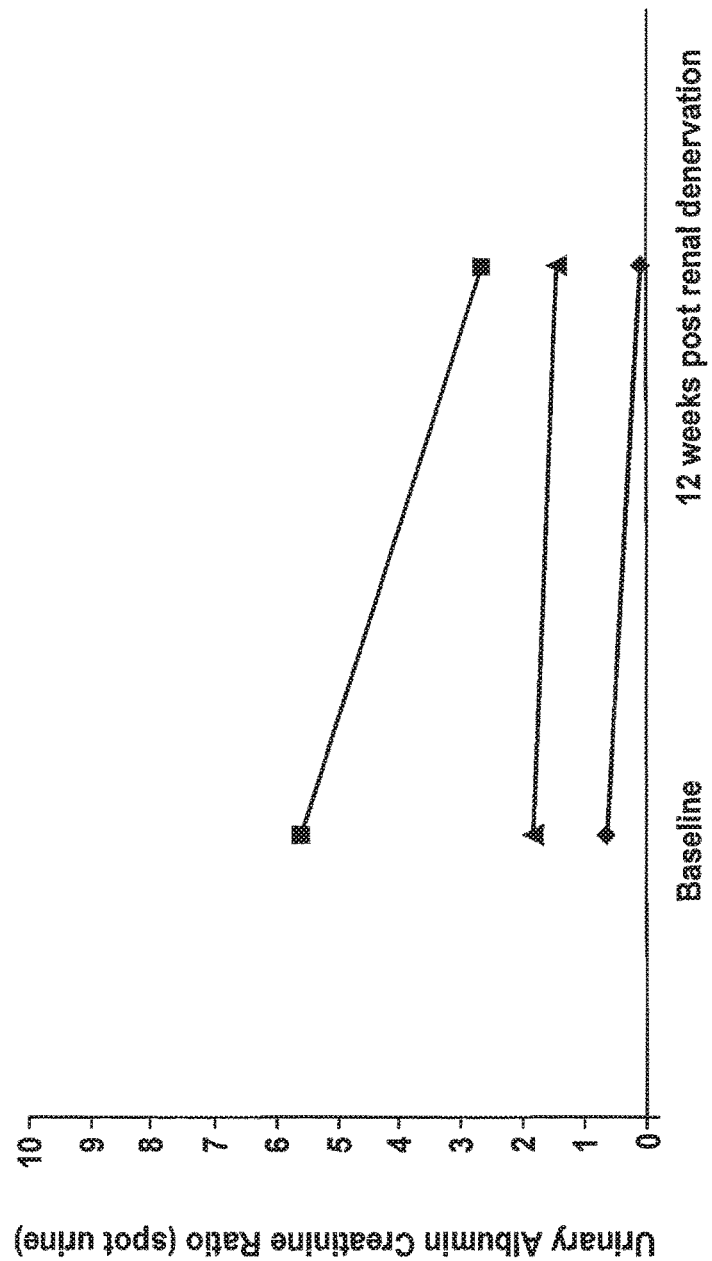
FIG. 28 shows changes in UACR for patients who underwent therapeutic renal neuromodulation.
Figure 29:
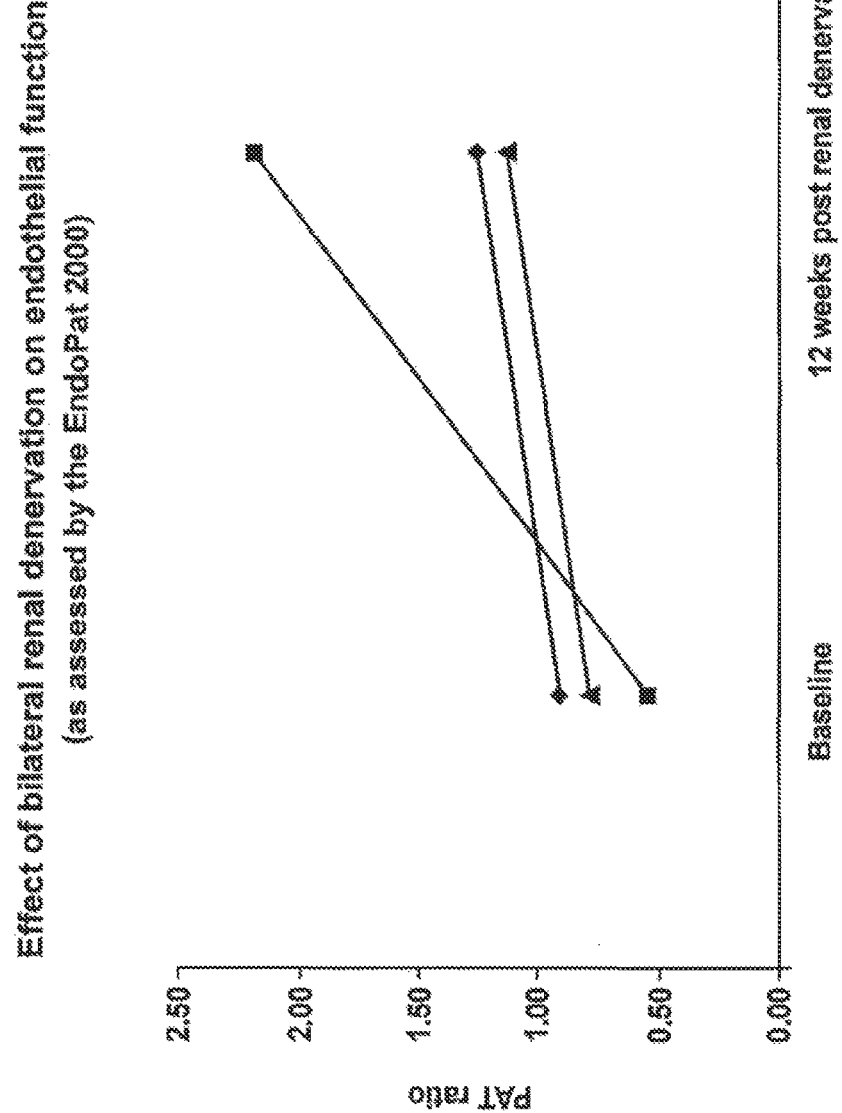
FIG. 29 shows changes in endothelial function for patients who underwent therapeutic renal neuromodulation.
Figure 30:
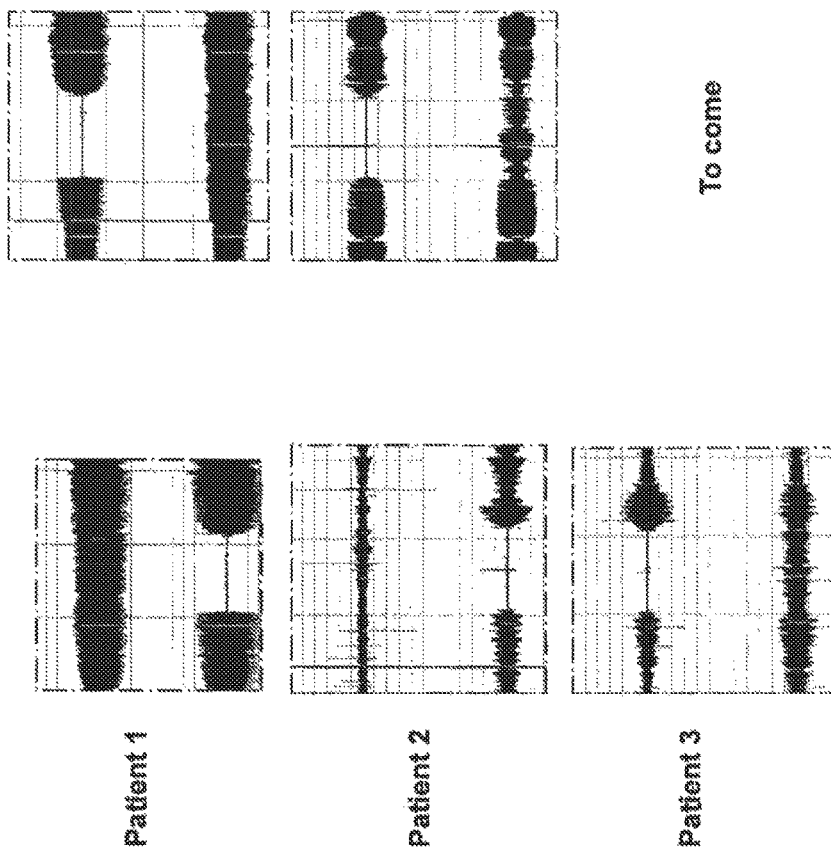
FIG. 30 shows a breakdown of the raw data related to endothelial function for each patient for patients who underwent therapeutic renal neuromodulation.

In particular, FIG. 19 shows changes in mean sitting office systolic blood pressure after 5 minutes of rest. FIG. 20 shows changes in a mean of 3 sitting office diastolic blood pressure measurements after 5 minutes of rest. FIG. 21 shows changes in a mean of 3 sitting office heart rate measurements after 5 minutes of rest. FIG. 22 shows effects on MSNA as assessed by microneurography. FIG. 23 shows the effects of bilateral renal denervation of body weight, and FIG. 24 shows the effects on fasting plasma glucose. FIG. 25 is a graph of changes in insulin sensitivity. FIG. 26 is a graph of changes in measured cystatin C. FIG. 27 shows the changes at 12 weeks post-treatment in creatinine clearance over a 24 hour urine sampling. FIG. 28 shows changes in UACR. FIG. 29 shows changes in endothelial function, and FIG. 30 shows a breakdown of the raw data related to endothelial function for each patient.

As shown below, Table 7 is a summary of results for a euglycaemic hyperinsulinaemic clamp test for the three patients at 3 months post-treatment. This test provides indices of insulin sensitivity

TABLE 6

Euglycaemic hyperinsulinaemic clamp data at baseline and
12 weeks following renal sympathetic denervation (n = 3).

|  | Baseline | | Week 12 | |
|---|---|---|---|---|
|  | Time 0 | Steady state | Time 0 | Steady State |
| Glucose (mmol/L) | 6.3 ± 0.6 | 5.0 ± 0.1 | 5.3 ± 0.7 | 5.0 ± 0.1 |
| C-Peptide (pmol/L) | 1359 ± 274 | 883 ± 234 | 1469 ± 375 | 1142 ± 310 |
| M (mg/kg/min) |  | 3.10 ± 0.88 |  | 3.84 ± 0.90* |
| M (mg/kg FFM/min) |  | 5.51 ± 1.70 |  | 6.85 ± 2.07 |

*P = 0.03 versus Baseline by paired t-test,
FFM = fat free mass as determined by DEXA
Note:
the higher the M value the better insulin sensitivity G. Safety, Efficacy, and Durability As disclosed herein, renal neuromodulation is expected to be a safe, effective, and durable method to reduce blood pressure, promote insulin sensitivity, and promote kidney function. In one particular example, the safety of renal neuromodulation was studied by imaging of the renal arteries in 38 patients by CT or MR angiography, a standard visualization technique which can identify changes in the vessel geometry. Although embodiments of the disclosed renal neuromodulation procedures disabled the renal nerves through the blood vessel wall, no significant changes were noted in the affected blood vessel walls within 6 months of the procedures.

An additional study on the durability of renal denervation followed patients up to 24 months post-treatment. Patients were enrolled based on having an elevated office systolic blood pressure (160 mmHg) despite taking at least three anti-hypertensive drug classes, one of which was a diuretic, at target or maximal tolerated dose. Patients were excluded if they had an estimated glomerular filtration rate (eGFR) of <45 mL/min/1.73 m$^2$, type 1 diabetes, or a known secondary cause of hypertension other than sleep apnea or chronic kidney disease. Patients with significant renovascular abnormalities were not permitted to undergo the intervention. This was assessed by various methods including angiography, MR angiography, CT angiography and duplex ultrasound. Such anatomical abnormalities included multiple main renal arteries, short length main renal artery and hemodynamically significant renal artery stenosis. Patients had to be over 18 years of age.

The primary efficacy endpoint of the study was change in office blood pressure. Patients had office blood pressure measurements performed in accordance with Joint National Committee (JNC) VII guidelines. Measurements were performed sitting, in triplicate, and then averaged. The primary safety assessments were based on physical examination, basic blood chemistries and anatomical assessment of the renal vasculature. Renal evaluations were performed via angiography in initial patients (at 14-30 days post procedure) and via renal MR angiography, CT angiography, or duplex scan at 6 months. Physicians could alter background blood pressure-lowering medication at any time for clinical reasons but were encouraged not to do so unless considered absolutely necessary, in order to carefully assess the effect of the procedure per se. This was more strictly applied during the initial 12 months of the follow-up study, less so after this time. Baseline measurements included physical examination, vital signs, basic blood chemistries and pregnancy testing as appropriate. Follow-up assessments occurred at 1, 3, 6, 12, 18 and 24 months. Assessment of routine biochemistry, including estimated glomerular filtration rate (eGFR, using the Modification of Diet in Renal Disease (MDRD) formula), was performed within the individual laboratories of participating hospitals.

The denervation procedure itself involved an endovascular catheter-based approach to disrupt renal sympathetic nerves using radiofrequency (RF) ablation applied via an electrode at the catheter tip. The central arterial tree was accessed via the femoral artery. The lumen of the main renal artery was catheterized. The Symplicity® Catheter (Ardian, Inc., Mountain View, Calif., USA) was connected to a RF generator and multiple RF treatments were applied in a manner devised to maximize renal sympathetic nerve disruption within the individual artery. Specifically, the first RF treatment was applied in the distal renal artery, the catheter was then retracted by 5 mm and rotated circumferentially before the energy was re-applied. This was continued until 4-6 treatments were applied within each renal artery and across the full circumference of the vessel. Each low-power treatment lasted up to two minutes. The first 10 patients underwent staged sequential procedures involving a single renal artery followed by the contralateral artery one month later. Subsequent patients underwent bilateral procedures in one session.

Blood pressure levels from baseline to the above timepoints were evaluated to calculate mean change as well as 95% confidence intervals. This was assessed by repeated measures analysis of variance with pair-wise comparison of significant values. A two-tailed paired t-test of p<0.05 was regarded as statistically significant. Multivariate stepwise backward regression analysis of key demographic and procedural characteristics that may predict increased SBP response were performed. Baseline variables entered into the model were: age, gender, race, body mass index, SBP, DBP, pulse pressure, heart rate, drug class, number of antihypertensive medications, eGFR, hypercholesterolemia and coronary artery disease. Change in eGFR was evaluated in comparison to baseline at various time-points using paired t-test. All statistical analysis was performed using SPSS version 15.0.

One-hundred fifty-three patients were treated in this open-label proof-of-concept study. Baseline characteristics of the study subjects including demographics and background medication are listed in Table 8. Mean baseline blood pressure values were 176/98±17/14 mmHg. Patients were taking an average of 5.0±1.4 antihypertensive drug classes. The median time from first to last RF energy delivery was 38 minutes, with an average of 4 ablations in each renal artery. There were no device malfunctions. Conscious sedation using IV narcotics and anxiolytics were commonly used to prevent and manage expected pain during the procedure. Episodes of bradycardia observed during the procedure were managed with administration of atropine in 10% (15/153) patients.

TABLE 7

Demographics of Treated Patients.

| Age ± SD | 57 ± 11 |
|---|---|
| Sex (female) | 39% |
| Ethnic origin (non-white) | 5% |
| Type 2 diabetes | 31% |
| CAD | 22% |
| Hyperlipidemia | 68% |
| eGFR (mL/min/1.73 m$^2$) | 83 ± 20 |

TABLE 7-continued

Demographics of Treated Patients.

| | |
|---|---|
| Heart Rate (bpm) | 73 ± 13 |
| Blood Pressure (mmHg) | 176/98 ± 17/15 |
| No. anti-HTN medications | 5.0 ± 1.4 |
| Diuretic | 95% |
| Aldosterone blocker | 25% |
| ACE inhibitor or ARB | 90% |
| Direct renin inhibitor | 14% |
| β-blocker | 81% |
| Calcium-channel blocker | 75% |
| Centrally acting sympatholytic | 35% |
| Vasodilator | 18% |
| Alpha-1 blocker | 20% |

CAD: coronary artery disease; eGFR: estimated glomerular filtration rate; ACE: angiotensin converting enzyme; ARB: angiotensin receptor blocker.

Figure 31A:
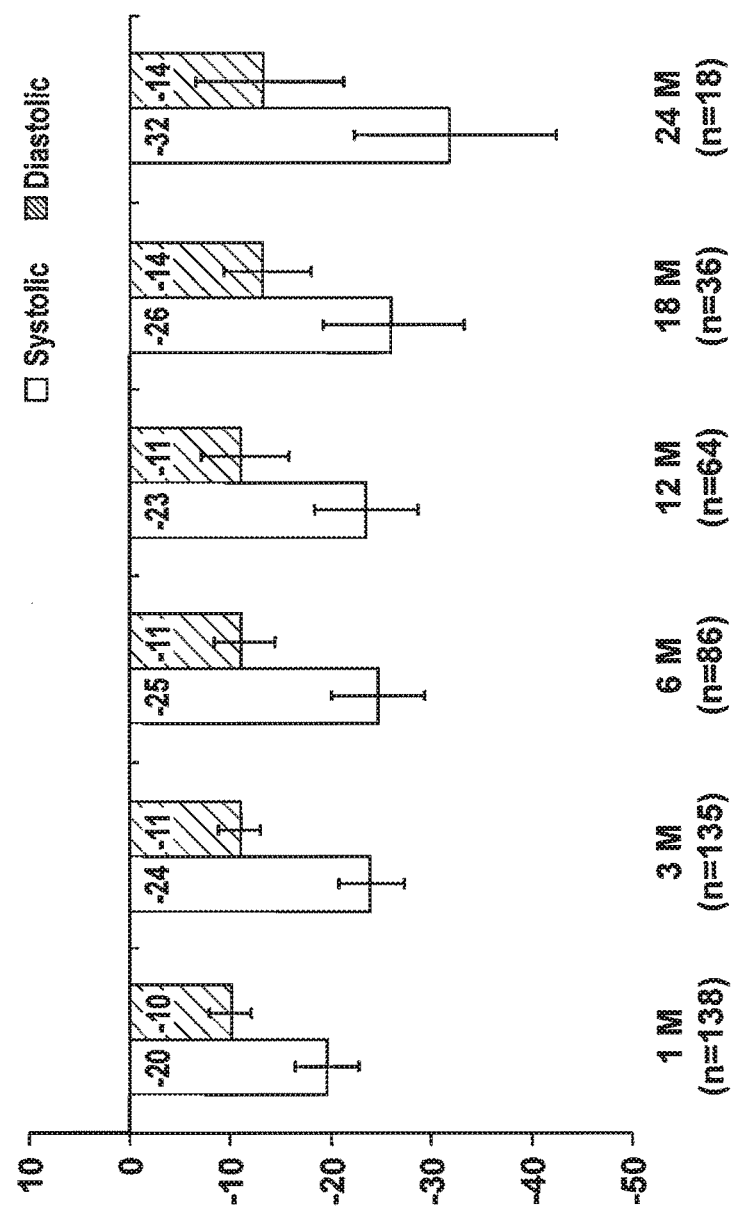
FIG. 31A is a graph showing the office BP data for patients who underwent therapeutic renal neuromodulation out to 24 months.

Ninety-two percent of patients had an office blood pressure reduction of at least 10 mmHg. Within patient changes in both systolic and diastolic blood pressure were highly significant (p<0.001) at all time-points post-procedure with BPs reduced on average by 20/10, 24/11, 25/11, 23/11, 26/14, and 32/14 mmHg at 1, 3, 6, 12, 18, and 24 months respectively (FIG. 31A). Mean systolic and diastolic blood pressure change following renal sympathetic denervation procedure over 24-months follow-up.

Significant independent predictors of greater SBP response on multivariate analysis were higher baseline SBP (P<0.0001) and use of central sympatholytic agents (P=0.018). All other baseline parameters fell out as non-significant on multivariate analysis.

Figure 31B:
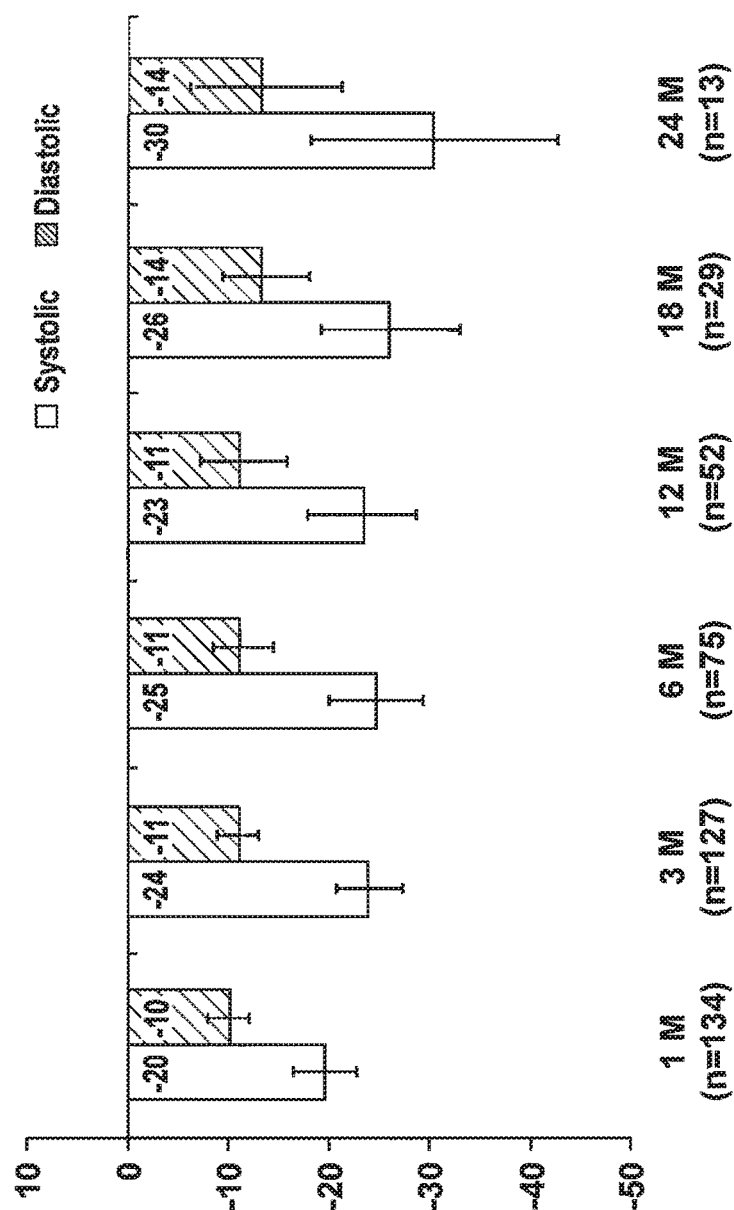
FIG. 31B is a graph showing the office BP for the patients of FIG. 31A with censored data for patients with increased hypertension pharmaceutical therapy.

The number of anti-hypertensive medications at last available follow-up was unchanged as compared to baseline (4.9 vs. 5.0; p=0.10). Twenty-seven patients were on a reduced number of medications at last follow-up compared with baseline; eighteen were on increased medications. Of the eighteen patients with medication increases, ten had their medications increased following drops in blood pressure, presumably in an attempt to achieve additional reductions in blood pressure. In order to ascertain the BP lowering effect of renal denervation in the absence of increased medications, office BP data censored following an increase in the number of medications is presented in FIG. 31B. Mean systolic and diastolic blood pressure change following renal sympathetic denervation procedure over 24-months following censoring for medication increases post-procedure. The magnitude of the mean blood pressure reduction in response to the procedure was unchanged when data from patients with increased anti-hypertension medications were censored.

The procedure was without complication in 97% (149/153) of patients. One patient experienced the renal artery dissection upon placement of the treatment catheter before RF energy delivery was delivered in that artery. The dissection was treated with renal artery stenting without any subsequent complication or delay in hospital discharge. Three other patients developed a pseudo-aneurysm/haematoma in the femoral access site, all were treated without any subsequent complication. In all cases, the procedure was performed with standard techniques for femoral artery access using commercially available introducers.

As mentioned, follow-up renal artery imaging was performed to evaluate structural abnormalities that may have occurred post-procedure in the treated renal arteries. Some minor focal renal artery irregularities due to minor spasm and/or edema were noted immediately following RF energy delivery. None were considered flow limiting at procedure termination. Of the short-term follow-up angiography performed in the first 20 patients no evidence of renal artery stenosis or abnormalities were noted in treated arteries. In the 81 patients with 6-month MRA, CTA, or duplex evaluation, no irregularities or stenoses at any treatment site were identified that were not present on pre-treatment angiography. One patient had a 6-month post-procedure CTA that identified progression of a pre-existing renal artery stenosis in the proximal portion of the renal artery. This stenosis was successfully stented; the location of the stenosis was quite proximal and well away from sites of RF energy application.

During the first year of follow-up, eGFR remained stable with a change at 1, 3, 6 and 12 months of +0.1 mL/min (95% CI: −2.8 to 3.0; N=112), −1.6 mL/min (95% CI: −4.3 to 1.1; N=102), −0.1 mL/min (95% CI: −2.9 to 2.8; N=87), and −2.9 mL/min (95% CI: −6.2 to +0.3; N=64), respectively. Estimated GFR data was only available on 10 patients at 2 years. In these 10 patients, eGFR changed by −16.0 mL/min/1.73 m$^2$ at 24 months post-procedure. Five of these 10 patients had spironolactone or other diuretic added after the first year of follow-up. In patients without newly added spironolactone or other diuretic, eGFR changed −7.8 mL/min/1.73 m$^2$ for an annualized change of −3.9 mL/min/1.73 m$^2$. In no cases did serum creatinine double, the patient develop Class IV chronic kidney disease, or require dialysis.

No patients reported symptomatic orthostatic hypotension. Six patients reported transient dizziness; no patients had any loss of consciousness. Three patients reported pitting oedema which was felt to be related to medication adjustment. This responded to conservative care, use of diuretics and/or reduction in minoxidil dose.

Bilateral flank pain was reported by a single patient. Extensive diagnostic evaluation did not identify a specific cause for this pain. It did respond to ibuprofen over a number of months, but eventually completely resolved. Three other patients reported intermittent or transient flank or kidney pain; all resolved with or without analgesic intervention.

The blood pressure reductions occurred in patients who, by definition, were refractory to standard medical therapies. Amongst this cohort, 92% of patients had a reduction in systolic BP. Multivariate analysis was able to discern two groups of patients likely to benefit from the denervation procedure: patients with the highest SBP at baseline and those using central sympatholytic agents (e.g., clonidine).

The persistence of overall blood pressure lowering out to two years is of clinical and patho-physiological relevance. In particular, sympathetic nerves which have been denervated via surgical approaches (most commonly in the organ transplantation setting) do appear to anatomically re-innervate, over a period of months. The findings of the study indicate that the initial blood pressure reduction observed out to 12 months persist to at least 24 months. Further, the magnitude of blood pressure lowering post-procedure at 24 months is no less than and appears to be numerically greater than that observed at 12 months.

The decline in renal function observed in this 24-month follow-up analysis is less than would be predicted based on the blood pressure response achieved, especially so over the first 12 months post-procedure prior to the introduction of diuretics which may worsen renal function. Accordingly, there may be an intrinsic beneficial effect of the procedure on the kidney to maintain renal function which is greater than that achieved via blood pressure reduction alone.

Another observation from this extended follow-up of renal denervation patients was the ongoing safety observed within the study. In this report a larger cohort of patients is exposed to a longer period of post-procedure follow-up without any major safety signals emerging. In particular, in the cohort of 81 patients with 6-month follow-up imaging, no cases of major de novo renal artery stenosis had occurred, and only one case of progression of an existing stenosis is described. Even with that single case, it cannot be determined whether this was specifically related to the interventional procedure or natural progression of a baseline stenosis. No cases of renal artery aneurysm, nor of cholesterol emboli were documented in this series. Furthermore, no late clinical sequelae (out to two years) could be attributed to development of renal artery stenosis.

V. Conclusion

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the words "herein," "above," and "below" and words of similar import, when used in this application, shall refer to this application as a whole and not to any particular portions of this application.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while process steps or functions are presented in a given order, alternative embodiments may perform functions in a different order, or functions may be performed substantially concurrently. The teachings of the disclosure provided herein can be applied to other systems, not only the systems described herein. Furthermore, the various embodiments described herein can be combined to provide further embodiments.

All of the references cited herein are incorporated by reference. Aspects of the disclosure can be modified, if necessary, to employ the systems, functions and concepts of the above references and applications to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. The following examples provide additional representative embodiments.

We claim:

1. A method, comprising:
positioning an electrode within a renal artery of a hypertensive human patient and proximate to renal nerves along the renal artery;
ablating the renal nerves via electrical energy from the electrode at a plurality of locations along a wall of the renal artery; and
removing the electrode from the patient after ablating the renal nerves,
wherein the patient achieves a decrease in systolic blood pressure of at least 10 mm Hg by three months as a result of ablating the renal nerves.

2. The method of claim 1 wherein the patient achieves a decrease in diastolic blood pressure of at least 5 mm Hg by three months after ablation of the renal nerves.

3. The method of claim 1 wherein the patient achieves a decrease in systolic blood pressure of at least 20 mm Hg by six months after ablation of the renal nerves.

4. The method of claim 1 wherein the patient achieves a decrease in systolic blood pressure of at least 25 mm Hg by six months after ablation of the renal nerves.

5. The method of claim 1 wherein the patient achieves a decrease in diastolic blood pressure of at least 10 mm Hg by six months after ablation of the renal nerves.

6. The method of claim 1 wherein the patient achieves a decrease in systolic blood pressure of at least 20 mm Hg by twelve months after ablation of the renal nerves.

7. The method of claim 1 wherein the patient achieves a decrease in systolic blood pressure of at least 20 mm Hg by eighteen months after ablation of the renal nerves.

8. The method of claim 1 wherein the patient achieves a decrease in systolic blood pressure of at least 25 mm Hg by eighteen months after ablation of the renal nerves.

9. The method of claim 1 wherein the patient achieves a decrease in systolic blood pressure of at least 25 mm Hg by twenty four months after ablation of the renal nerves.

10. The method of claim 1 wherein the patient achieves a decrease in systolic blood pressure of at least 30 mm Hg by twenty four months after ablation of the renal nerves.

11. The method of claim 1 wherein the patient achieves a decrease in systolic blood pressure of at least 30 mm Hg by twenty four months after ablation of the renal nerves.

12. The method of claim 1 wherein the patient achieves a decrease in systolic blood pressure at twenty four months after ablation of the renal nerves greater than the observed decrease in systolic blood pressure at twelve months after modulation.

13. The method of claim 1 wherein the patient achieves a decrease in diastolic blood pressure at twenty four months after ablation of the renal nerves greater than the observed decrease in diastolic blood pressure at twelve months after modulation.

14. The method of claim 1 wherein the patient has a baseline blood pressure before treatment of at least about 160 mm Hg.

15. The method of claim 1 wherein the electrode is one of a plurality of bipolar electrodes carried by an expandable balloon, and wherein:
positioning an electrode within a renal artery of a hypertensive human patient comprises positioning the balloon at a distal portion of the renal artery and transforming the balloon from a low-profile delivery configuration into a deployed configuration such that the bipolar electrodes carried by the balloon are positioned in contact with treatment locations along the wall of the renal artery; and
ablating the renal nerves comprises delivering electrical energy via the bipolar electrodes to the renal nerves along the renal artery.

16. The method of claim 1 wherein:
the electrode is one of a plurality of electrodes arranged along an elongated member, and further wherein the elongated member is transformable between (a) a low-profile delivery arrangement for intravascularly passage to a target site within the renal artery and (b) a deployed arrangement in which the elongated member assumes a generally helical shape and is configured to contact the wall of the renal artery;

positioning an electrode within a renal artery of a hypertensive human patient comprises transforming the elongated member from the delivery arrangement into the deployed arrangement such that the elongated member assumes the generally helical shape and the plurality of electrodes carried thereon are positioned in contact with treatment locations arranged in a helical pattern along the wall of the renal artery; and ablating the renal nerves comprises delivering electrical energy via the plurality of electrodes to the renal nerves along the renal artery.

\* \* \* \* \*